(12) United States Patent
Kuk et al.

(10) Patent No.: US 12,686,001 B2
(45) Date of Patent: Jul. 21, 2026

(54) P-N HETEROJUNCTION PHOTOCATALYST, AIR PURIFIER INCLUDING THE SAME, AND METHOD OF PREPARING THE P-N HETEROJUNCTION PHOTOCATALYST

(71) Applicant: Samsung Electronics Co., Ltd., Suwon-si (KR)

(72) Inventors: Su Keun Kuk, Suwon-si (KR); Hyun Chul Lee, Suwon-si (KR); Sang Min Ji, Suwon-si (KR); Sungwoo Kang, Suwon-si (KR); Dong Sik Yang, Suwon-si (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 525 days.

(21) Appl. No.: 18/319,760

(22) Filed: May 18, 2023

(65) Prior Publication Data

US 2024/0173710 A1 May 30, 2024

(30) Foreign Application Priority Data

Nov. 25, 2022 (KR) ......................... 10-2022-0160725

(51) Int. Cl.
*B01J 35/39* (2024.01)
*A61L 9/20* (2006.01)
(Continued)

(52) U.S. Cl.
CPC .............. *B01J 35/39* (2024.01); *A61L 9/205* (2013.01); *B01J 35/23* (2024.01); *B01J 35/40* (2024.01);
(Continued)

(58) Field of Classification Search
CPC ... B01J 35/39; B01J 35/23; B01J 35/40; B01J 21/063; B01J 19/123; B01J 35/393;
(Continued)

(56) References Cited

U.S. PATENT DOCUMENTS 10,315,191 B2 * 6/2019 Leung .................... B01J 19/127
2022/0280923 A1 9/2022 Ji et al.

FOREIGN PATENT DOCUMENTS

CN 101618332 A 1/2010
CN 106732737 A 5/2017
(Continued)

OTHER PUBLICATIONS

Mechanistic insights into nano-regional heterostructures for photocatalytic and photoelectrochemical applications. Nanyang Environment and Water Research Institute. (Year: 2020).*
(Continued)

*Primary Examiner* — Coris Fung
*Assistant Examiner* — Remy Frederic Lalisse
(74) *Attorney, Agent, or Firm* — CANTOR COLBURN LLP

(57) ABSTRACT

A p-n heterojunction photocatalyst, an air purifier including the p-n heterojunction photocatalyst, and a method of preparing the p-n heterojunction photocatalyst. The p-n heterojunction photocatalyst includes a granule type composite which includes: first compound particles; and second compound particles on at least a portion of surfaces of the first compound particles, wherein the composite has a size of about 0.9 μm to about μm based on a major axis, a standard deviation of the size is about ±0.9 μm or less, and upon exposure to energy irradiation, the composite generates a reactive oxygen species of singlet oxygen ($^1O_2$) to induce photolysis of gaseous pollutants.

16 Claims, 30 Drawing Sheets

P-N HETEROJUNCTION PHOTOCATALYST

(51) Int. Cl.

| | | |
|---|---|---|
| *B01J 35/23* | (2024.01) |
| *B01J 35/40* | (2024.01) |
| *A61L 101/02* | (2006.01) |

(52) U.S. Cl.
CPC ....... *A61L 2101/02* (2020.08); *A61L 2209/14* (2013.01)

(58) Field of Classification Search
CPC .. A61L 9/205; A61L 2101/02; A61L 2209/14; A61L 2209/11; B01D 2255/802; B01D 2259/804; B01D 2258/06; B01D 53/885; C02F 1/725; C02F 2305/10; Y10S 977/811
See application file for complete search history.

(56) References Cited

FOREIGN PATENT DOCUMENTS

| | | |
|---|---|---|
| CN | 111229217 A | 6/2020 |
| CN | 111558385 A | 8/2020 |
| KR | 20040009316 A | 1/2004 |
| KR | 101724629 B1 | 4/2017 |
| KR | 20190087913 A | 7/2019 |
| KR | 20220003372 A | 1/2022 |
| KR | 20220126157 A | 9/2022 |

OTHER PUBLICATIONS

Huang, H., et al., In Situ Construction of Dye-Sensitized BiOCl/Rutile-TiO2 Nanorod Heterojunctions with Highly Enhanced Photocatalytic Activity for Treating Persistent Organic Pollutants. Inorganic Chemistry. (Year: 2021).*

Liao, X et al., Construction of BiOl/TiO2 flexible and hierarchical S-scheme heterojunction nanofibers membranes for visible-light-driven photocatalytic pollutants degradation. Science of the Total Environment. (Year: 2021).*

Schreck, Murielle et al., "Photocatalytic Gas Phase Reactions," Chemistry of Materials, copyright 2019 American Chemical Society, vol. 31, pp. 597-618, 22 pp. , DOI: 10.1021/acs.chemmater.8b04444.

Nosaka, Yoshio et al., "Generation and Detection of Reactive Oxygen Species in Photocatalysis", Chemical Reviews, copyright 2017 American Chemical Society, vol. 117, pp. 11302-11336, 35 pp., DOI: 10.1021/acs.chemrev.7b00161.

Wang, Jianmin et al., "In situ fabrication of a-Fe203/CaFe204 p-n heterojunction with enhanced VOCs photodegradation activity," Advanced Powder Technology, copyright 2019, vol. 30, pp. 590-595, 6 pp., https://doi.org/10.1016/j.apt.2018.11.027.

Zhang, Yan et al., "TiO2/BiOl p-n junction-decorated carbon fibers as weavable photocatalyst with UV-vis photoresponsive for efficiently degrading various pollutants," Chemical Engineering Journal vol. 415, copyright 2021, 11 pp., https://doi.org/10.1016/j.cej.2021.129019.

* cited by examiner

P–N HETEROJUNCTION PHOTOCATALYST

*FFA: FURFURYL ALCOHOL     *6HP-one: 6-HYDROXY-(2H)-PYRAN-3-ONE

P-N HETEROJUNCTION PHOTOCATALYST, AIR PURIFIER INCLUDING THE SAME, AND METHOD OF PREPARING THE P-N HETEROJUNCTION PHOTOCATALYST

CROSS-REFERENCE TO RELATED APPLICATION

This application claims priority to Korean Patent Application No. 10-2022-0160725, filed on Nov. 25, 2022, in the Korean Intellectual Property Office, and all the benefits accruing therefrom under 35 U.S.C. § 119, the disclosure of which in its entirety is herein incorporated by reference.

BACKGROUND

1. Field

The disclosure relates to a p-n heterojunction photocatalyst, an air purifier including the p-n heterojunction photocatalyst, and a method of manufacturing the p-n heterojunction photocatalyst.

2. Description of the Related Art

Conventionally, to remove pollutants from the air a method of adsorbing/removing gaseous pollutants may include applying an adsorbent (for example, activated carbon) having a large specific surface area to an air cleaning filter. However, in the method of adsorbing/removing gaseous pollutants, the adsorbed gaseous pollutants upon desorption may cause secondary pollution. Moreover, the method may require a separate regeneration process such as heating an adsorbent to a high temperature in order to reuse the adsorbent, and the performance of the adsorbent may rapidly degrade in the presence of moisture and high temperature.

In order to improve upon such limitations to such a filter, research is being conducted on photocatalysts that can decompose pollutants by photooxidation at room temperature using light as an energy source, thereby, removing the pollutants or decomposing the pollutants into harmless substances, e.g., water or carbon dioxide.

With many photocatalysts, hydroxy radicals (·OH), which are generated by moisture in the air, are used as a reactive oxygen species (ROS) during the decomposition of the gaseous pollutants. However, since hydroxyl radicals (·OH) have a relatively short lifetime of about 20 milliseconds (ms) and a diffusion distance of about 1 mm, the decomposition activity of the photocatalyst for gas pollutants in the air is somewhat limited.

Therefore, there is a need for the development of a photocatalyst using a different ROS to remove gaseous pollutants, an air purifier including the photocatalyst, and a method of preparing the photocatalyst.

SUMMARY

An aspect is to provide a p-n heterojunction photocatalyst which photolyzes gaseous pollutants utilizing singlet oxygen ($^1O_2$) as a reactive oxygen species (ROS), the ROS having a relatively longer lifetime and greater diffusion distance in the gas phase than, e.g., hydroxy radicals.

Another aspect is to provide an air purifier including a photocatalyst filter which includes the p-n heterojunction photocatalyst.

Still another aspect is to provide a method of preparing the p-n heterojunction photocatalyst.

Additional aspects will be set forth in part in the description which follows and, in part, will be apparent from the description, or may be learned by practice of the presented embodiments of the disclosure.

According to an aspect, a p-n heterojunction photocatalyst includes a composite, e.g., a granule type composite, the composite includes first compound particles, and second compound particles on at least a portion of surfaces of the first compound particles, wherein the composite has a size of about 0.9 micrometers (μm) to about 5 μm based on a major axis, a standard deviation of the size is about ±0.9 μm or less, and upon exposure to energy irradiation, the composite generates a reactive oxygen species of singlet oxygen ($^1O_2$) to induce photolysis of gaseous pollutants.

According to another aspect, an air purifier includes a photocatalyst filter which includes the above-described p-n heterojunction photocatalyst.

According to still another aspect, a method of preparing a p-n heterojunction photocatalyst includes adding first compound particles to one or more second compound precursor solutions to obtain a mixture, and drying the mixture to prepare a composite including the first compound particles and second compound particles on at least a portion of surfaces of the first compound particles, wherein the composite has a size of about 1 μm to about 5 μm based on a major axis, a standard deviation of the size is about ±0.9 μm or less, and upon exposure to energy irradiation, the composite generates a reactive oxygen species of singlet oxygen ($^1O_2$) to induce photolysis of gaseous pollutants.

DETAILED DESCRIPTION

Figure 1:
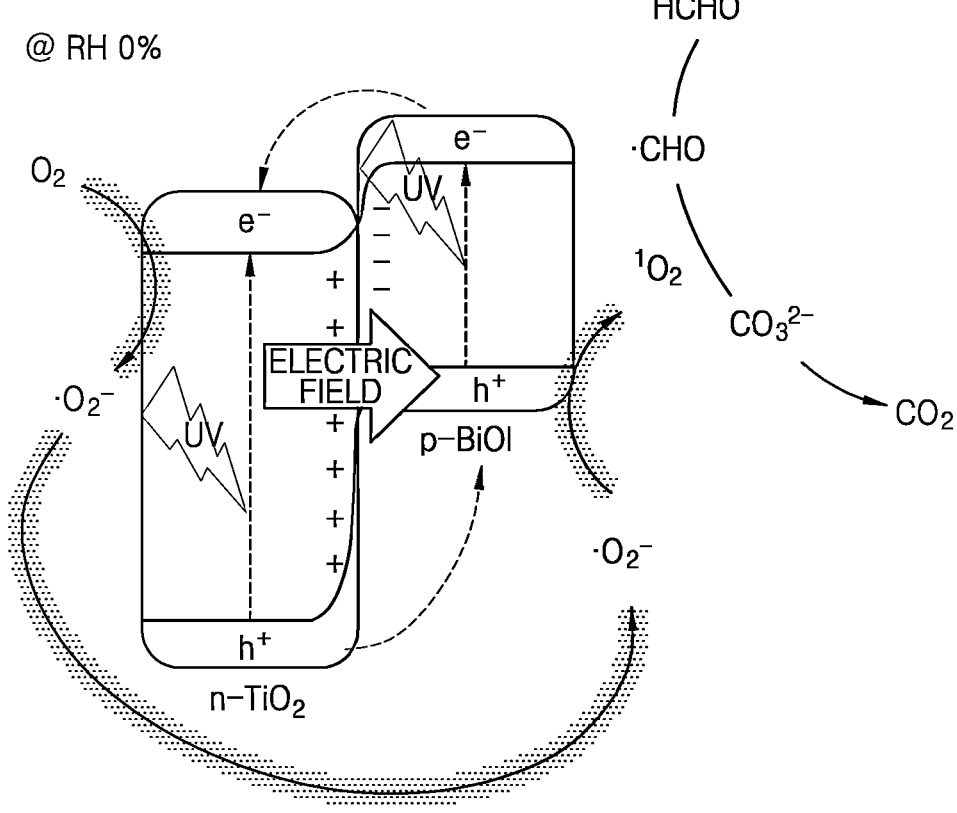
FIG. 1 is a schematic diagram for describing an operating principle of a p-n heterojunction photocatalyst according to one embodiment.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects.

The terminology used herein is for the purpose of describing particular embodiments only and is not intended to be limiting. As used herein, the singular forms "a," "an," and "the" are intended to include the plural forms, including "at least one," unless the content clearly indicates otherwise. "At least one" is not to be construed as limiting "a" or "an." "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

It will be understood that when an element is referred to as being "on" another element, it can be directly on the other element or intervening elements may be present therebetween. In contrast, when an element is referred to as being "directly on" another element, there are no intervening elements present.

Unless otherwise stated, all percentages, parts, ratios, and the like are by weight. In addition, when an amount, concentration, or other value or parameter is given as either a range, preferred range or a list of upper preferable values and/or lower preferable values, this is to be understood as specifically disclosing all ranges formed from any pair of any upper range limit or preferred value and any lower range limit or preferred value, regardless of whether ranges are separately disclosed.

"About" or "approximately" as used herein is inclusive of the stated value and means within an acceptable range of deviation for the particular value as determined by one of ordinary skill in the art, considering the measurement in question and the error associated with measurement of the particular quantity (that is, the limitations of a measurement system). For example, "about" may mean 5% of the stated value.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized. or overly formal sense unless expressly so defined herein.

Embodiments are described herein with reference to cross section illustrations that are schematic illustrations of ide-alized embodiments. As such, the shapes of the illustrations as a result, for example, of manufacturing techniques and/or tolerances, may be changed. Thus, embodiments described herein should not be construed as limited to the particular shapes of regions as illustrated herein but are to include deviations in shapes that result, for example, from a manu-facturing process. For example, a region illustrated or described as flat may, typically, have rough and/or nonlinear features. Moreover, sharp angles that are illustrated may be rounded. Thus, the regions illustrated in the drawings are schematic in nature and their shapes are not intended to illustrate the precise shape of a region and are not intended to limit the scope of the present claims.

A p-n heterojunction photocatalyst, an air purifier includ-ing the p-n heterojunction photocatalyst, and a method of manufacturing the p-n heterojunction photocatalyst accord-ing to embodiments will be described in more detail.

A photocatalyst is a material that upon exposure to energy, e.g., light of a certain energy (wavelength range) electrons and holes may be formed to induce an oxidation/reduction reaction. One application of a photocatalyst is the removal or degradation of gaseous pollutants from a gas stream or flow by contacting the gas with the photocatalyst resulting in a gas component (pollutant) that is degraded by the oxida-tion/reduction reaction.

In general photocatalysts, upon exposure to light may generate hydroxy radicals (·OH) from the moisture present in air (gas flow) that are then used as a reactive oxygen species (ROS). However, because hydroxyl radicals (·OH) have a relatively short lifetime of about 20 ms and a diffusion distance of about 1 mm, the decomposition activity of such photocatalysts to degrade gas pollutants is somewhat limited.

A photocatalyst according to an embodiment is a p-n heterojunction photocatalyst. The p-n heterojunction photo-catalyst refers to a photocatalyst in which electrons may be transferred between a p-type photocatalyst and an n-type photocatalyst due to a p-n heterojunction.

The p-n heterojunction photocatalyst according to one embodiment includes a composite including first compound particles and second compound particles on at least a portion of surfaces of the first compound particles.

The composite has a size of about 0.9 micrometers ($\mu$m) to about 5 $\mu$m based on a major axis, and a standard deviation of the size may be about ±0.9 $\mu$m. For example, based on the major axis, the composite has a size of about 0.91 $\mu$m to about 4.95 $\mu$m, a size of about 0.92 $\mu$m to about 4.90 $\mu$m, a size of about 0.93 $\mu$m to about 4.85 $\mu$m, a size of about 0.94 $\mu$m to about 4.80 $\mu$m, a size of about 0.95 $\mu$m to about 4.75 $\mu$m, a size of about 0.95 $\mu$m to about 4.70 $\mu$m, or a size of about 0.95 $\mu$m to about 4.66 $\mu$m. For example, the standard deviation of the size may be about ±0.89 $\mu$m, about ±0.88 $\mu$m, about ±0.87 $\mu$m, about ±0.86 $\mu$m, or about ±0.85 $\mu$m. The size of the composite may be measured using a particle size analyzer or may be measured from a transmis-sion electron microscope (TEM) or scanning electron micro-scope (SEM) image. Alternatively, dynamic light-scattering may be used to count the number of particles in each particle size range, and then the size of the composite may be obtained through calculation.

The composite may be a granule type composite. The granular composite may have a spherical shape, a tube shape, a fiber shape, a rod shape, a sheet shape, a flower shape, a flake shape, a belt shape, or a combination thereof. However, the disclosure is not limited thereto, and the granular composite may be a granule type composite having various shapes.

The first compound particles may be an n-type compound, and the second compound particles may be a p-type com-pound. Such characteristics may be confirmed through a Mott-Schottky plot.

The first compound particles may include $TiO_2$, $BiVO_4$, ZnO, $WO_3$, CdS, $BaTiO_3$, or a combination thereof. For example, the first compound particles may be metal oxide particles. For example, the first compound particles may include $TiO_2$, $BiVO_4$, ZnO, $WO_3$, or a combination thereof.

The second compound particles may include BiOI, $Cu_2O$, CuO, NiO, $BiFeO_3$, $LaFeO_3$, GaP, or a combination thereof. For example, the second compound particles may be metal oxide particles. For example, the second compound particles may include BiOI, $Cu_2O$, CuO, NiO, or a combination thereof.

Upon exposure to energy irradiation, the composite gen-erates a reactive oxygen species (ROS) of singlet oxygen ($^1O_2$) to induce photolysis of gaseous pollutants. The gas-eous pollutant may include, for example, a volatile organic compound (VOC), nitrogen oxide (NOx), sulfur oxide ($SO_x$), ammonia ($NH_3$), or a malodorous substance. Examples of the VOC include 1,3-butadiene, carbon tetra-chloride, benzene, trichloroethylene (TCE), formaldehyde (HCHO), ethylbenzene, chloroform, toluene, or n-hexane. It is to be understood, that the gaseous pollutant is not limited to the compounds listed above.

FIG. 1 is a schematic diagram for describing an operating principle of a p-n heterojunction photocatalyst according to one embodiment.

As shown in FIG. 1, a p-n heterojunction photocatalyst in which n-type $TiO_2$ as first compound particles and p-type BiOI as second compound particles are positioned adjacent to, and preferably, in contact with the other is schematically illustrated. Upon exposure of the photocatalyst to light (ultraviolet (UV) light) having an energy that is higher than or equal to a band gap energy of n-type $TiO_2$ as the first compound particles and p-type BiOI as the second com-pound particles, electrons transition from a valence band (VB) to a conduction band, and electron ($e^-$) and hole ($h^+$) pairs are generated. In this case, in a p-n heterojunction, holes ($h^+$) generated in a VB of n-type $TiO_2$ as the first compound particle move to a VB of p-type BiOI of the second compound particles, electrons ($e^-$) generated in a conduction band of p-type BiOI move to the VB of n-type $TiO_2$ as the first compound particles. As a result, ROS of singlet oxygen ($^1O_2$) is generated from oxygen in the air to a greater extent than a hydroxyl radical (·OH) being generated from moisture in the air. In may instances, a p-n heterojunction photocatalyst according to one embodiment produces little or no hydroxy radical as is described in more detail below.

The p-n heterojunction photocatalyst described herein utilizes singlet oxygen ($^1O_2$), which has a relatively long lifetime of about 54 milliseconds (ms) and a diffusion distance of about 2.7 mm in a gas phase under a low humidity or dry condition. The generated singlet oxygen can then photolyze gaseous pollutants, for example, a VOC.

Figure 2:
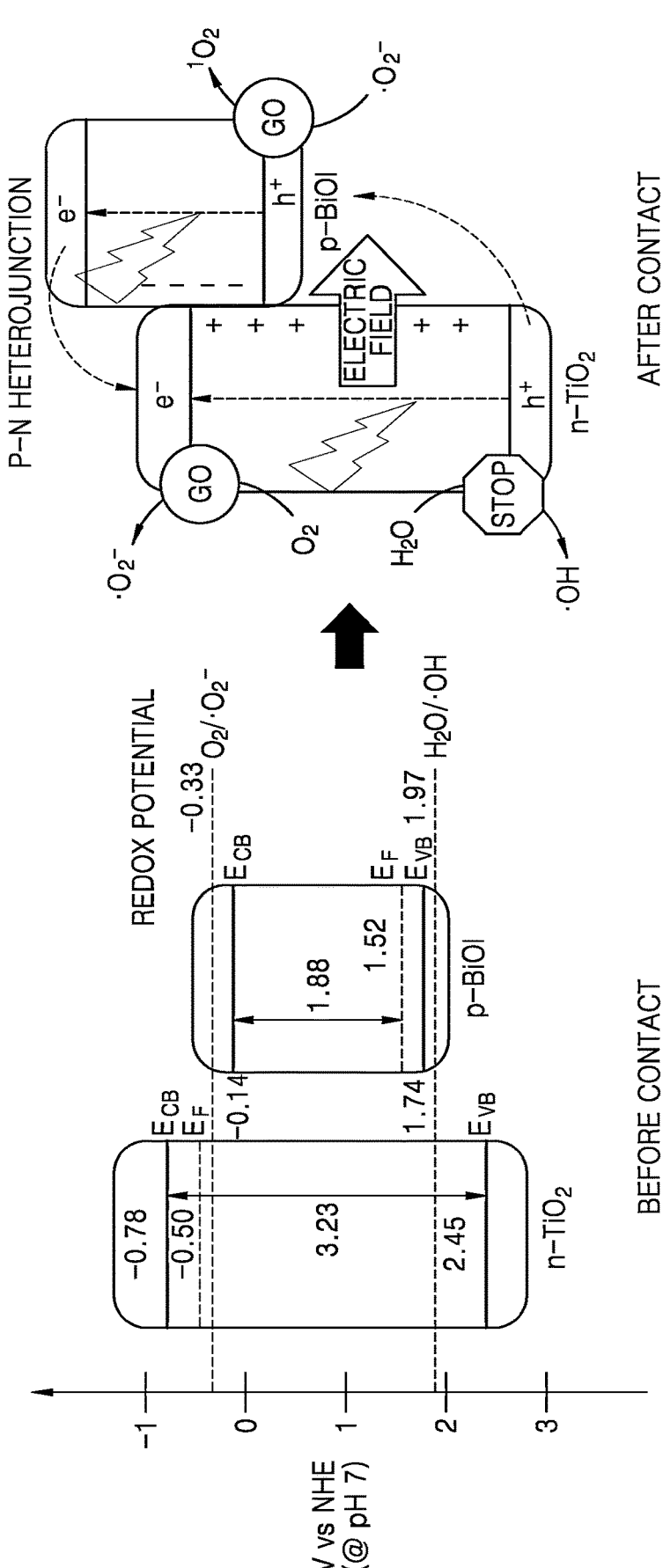
FIG. 2 is a schematic diagram showing reactive oxygen species (ROS) generation and ·OH generation oxidation potentials V (vs NHE@pH 7) before and after contact between first compound particles and second compound particles of a p-n heterojunction photocatalyst according to one embodiment.

FIG. 2 is a schematic diagram showing reactive ROS generation and ·OH generation oxidation potentials V (vs NHE@pH 7) before and after contact between the first compound particles and the second compound particles of the p-n heterojunction photocatalyst according to one embodiment. VBs of the first compound particles and the second compound particles may be confirmed through an X-ray photoelectron spectroscopy (XPS)-VB experiment.

Referring to FIG. 2, prior to contact between the first compound particles and the second compound particles of the p-n heterojunction photocatalyst, p-type BiOI as the second compound particles has an ·OH generation oxidation potential of about 1.97 V (vs NHE) in a VB. However, after contact between the first compound particles and the second compound particles, holes generated in n-type $TiO_2$ as the first compound particles in the p-n heterojunction move to a VB of p-type BiOI, and thus, the ·OH generation oxidation potential is lower than an energy level required to oxidize water.

Accordingly, in the p-n heterojunction photocatalyst according to one embodiment, a hydroxy radical (·OH) generated from moisture in the air is not generated as an ROS, and electrons ($e^-$) accumulated in a conduction band of n-type $TiO_2$ as the first compound particles are used to reduce oxygen to generate singlet oxygen ($^1O_2$).

The second compound particles of the p-n heterojunction photocatalyst according to one embodiment may have an ·OH generation oxidation potential of about 1.97 V or less (vs NHE) in a VB.

The composite of the p-n heterojunction photocatalyst according to one embodiment may be a structure in which surfaces of the first compound particles are negatively charged, and the second compound particles which are positively charged are self-assembled on the negatively charged surfaces of the first compound particles through an electronic interaction. In the composite, because the first compound particles and the second compound particles contact one another or are bonded though an electronic interaction, many contact surfaces may be formed between the first compound particles and the second compound particles to form a self-assembled structure. In comparison, if the first compound particles and the second compound particles are simply presented as a mixture (resulting in a form in which the particles are spaced apart from the other), the number of contact surfaces between the two particles is significantly reduced, and thus, an electrical interaction between the two particles is also reduced.

The surface charges of the first compound particles and the second compound particles is important in forming the composite, and are related in-part to a solvent used in synthesizing the composite, pH, and the like. For example, when the first compound particles are $TiO_2$ particles and the composite is synthesized at a pH of about 2 to about 3, surfaces of the $TiO_2$ particles are positively charged. On the other hand, if the pH is gradually increased to about 5, the surfaces of the $TiO_2$ particles become more negatively charged, a structure is formed in which the second compound particles that are positively charged, for example, BiOI particles, self-assemble on the negatively charged surfaces of the $TiO_2$ particles, e.g., through an electronic interaction. The surface charges of the first compound particles have a potential that is equal to a zeta potential, and the zeta potential may be obtained through a phase analysis light-scattering measurement.

Exposure of the composite to energy may include at least one of light energy, electrical energy, ion energy, and thermal energy. Light energy may be light energy in a range from a UV to visible. Ion energy may be plasma energy. Thermal energy may supply with infrared (IR) light.

The composite may have photolytic activity in a UV wavelength region. The composite may absorb UV light to cause a photocatalytic reaction. In the photocatalytic reaction, electrons and holes move between the first compound particles and the second compound particles to induce generation of singlet oxygen ($^1O_2$) as a ROS.

For example, when the composite is a $TiO_2$/BiOI composite, a peak of Ti2p binding energy, as measured by X-ray photoemission spectroscopy (XPS) may be shifted in a positive direction with respect to a peak of Ti2p binding energy of a $TiO_2$ photocatalyst. In the composite, a peak of Bi4f binding energy, as measured by XPS, may be shifted in a negative direction with respect to a peak of Bi4f binding energy peak of the $TiO_2$ photocatalyst. As a result, electrons may move in the composite according to a difference in electronegativity between the elements of titanium and bismuth constituting the composite.

The first compound particles of the composite may be primary particles, or secondary particles in which a plurality of primary particles are aggregated, and the second compound particles may be primary particles.

The first compound particles may be secondary particles in which a plurality of primary particles are aggregated, the second compound particles may be primary particles, and the composite may be a structure including the first compound particles with the second compound particles bound to the surfaces of the first compound particles.

Based on a major axis, a primary particle size of the first compound particles may be in a range of about 20 nanometers (nm) to about 30 nm, may be in a range of, for example, about 20 nm to about 29 nm, may be in a range of, for example, about 20 nm to about 28 nm, may be in a range of, for example, about 20 nm to about 27 nm, may be in a range of, for example, about 20 nm to about 26 nm, or may be in a range of, for example, about 20 nm to about 25 nm.

Based on a major axis, a secondary particle size of the first compound particles may be in a range of about 0.9 μm to about 5 μm, may be in a range of, for example, about 0.91 μm to about 5 μm, may be in a range of, for example, about 0.92 μm to about 5 μm, may be bin a range of, for example, about 0.93 μm to about 5 μm, may be in a range of, for example, about 0.94 μm to about 5 μm, or may be in a range of, for example, about 0.95 μm to about 5 μm.

The second compound particles may have a size of a nanometer scale or less.

The size of the first compound particles and the second compound particles may be measured using a particle size analyzer or may be measured from a TEM image or a SEM image. Alternatively, dynamic light-scattering may be used and data is analyzed to count the number of particles in each particle size range from which the size may be obtained by calculation.

With respect to the total weight of the composite, a content of the first compound particles may be in a range of about 50 weight percent (wt %) to about 95 wt %, may be in a range of, for example, about 50 wt % to about 90 wt %, may be in a range of, for example, about 60 wt % to about 90 wt %, or may be in a range of, for example, about 70 wt % to about 90 wt %.

With respect to the total weight of the composite, a content of the second compound particles may be in a range of about 5 wt % to about 50 wt %, may be in a range of, for example, about 10 wt % to about 50 wt %, may be in a range of, may be in a range of, for example, about 10 wt % to about 40 wt %, or may in a range of, for example, about 10 wt % to about 30 wt %.

For at least the reasons described, it is possible to provide a p-n heterojunction photocatalyst that effectively photolyzes gaseous pollutants utilizing singlet oxygen ($^1O_2$) as an ROS having a relatively long lifetime and greater diffusion distance in the gas phase that is within a content range of the first compound particles and the second compound particles.

A photocatalyst filter according to another embodiment may include the above-described p-n heterojunction photocatalyst.

A photocatalyst filter 100 and an air purifying system including the photocatalyst filter according to embodiments will be described in more detail with reference to FIGS. 13 to 17.

Figure 13:
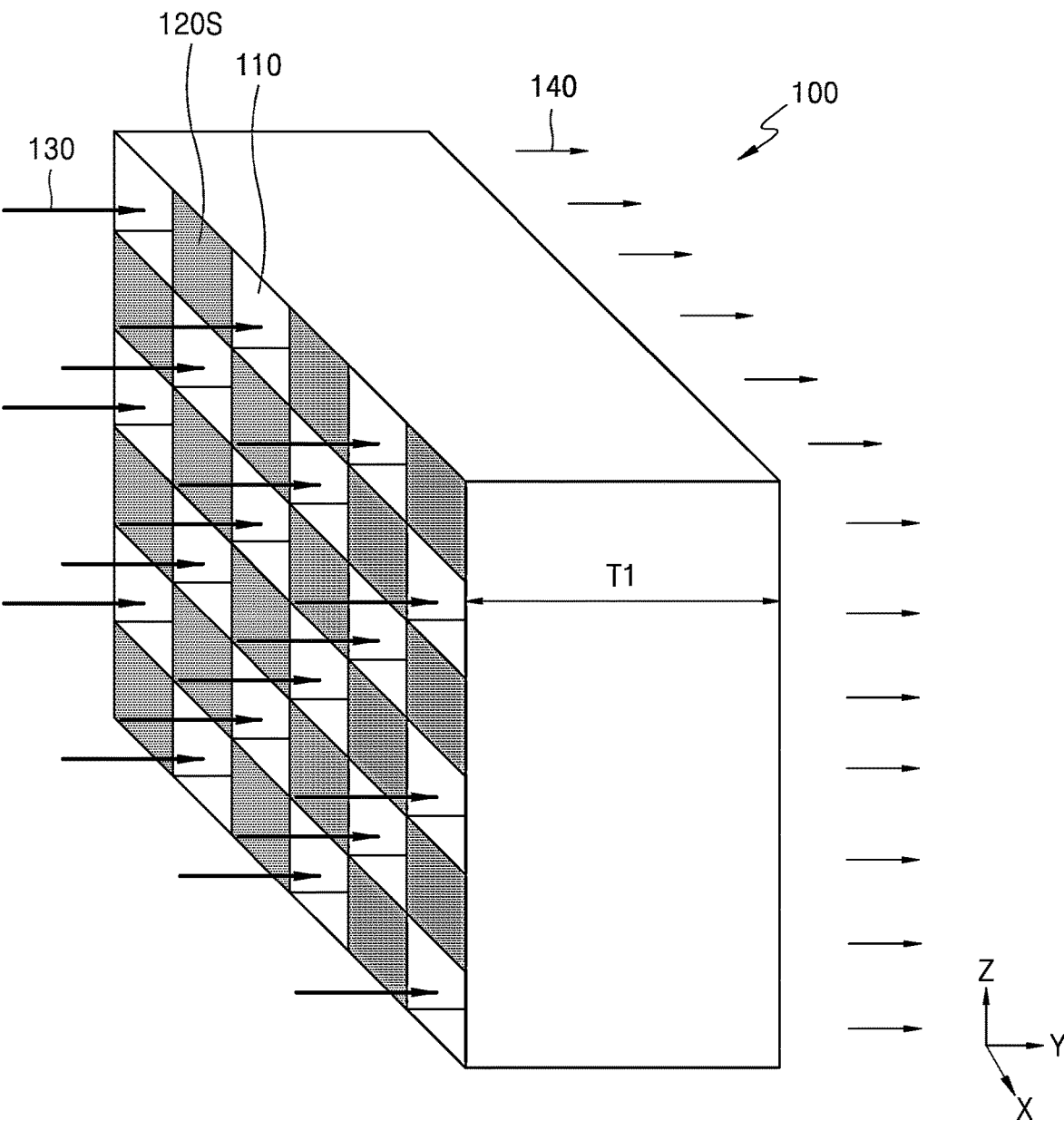
FIG. 13 is a schematic view of a photocatalyst filter according to one embodiment.

Referring to FIG. 13, the photocatalyst filter 100 includes an inlet surface through which unpurified air 130 is introduced and an outlet surface through which purified air 140 is discharged. The unpurified air 130 may include the undesired gaseous pollutants.

The photocatalyst filter 100 has a thickness T1 defined in a direction (Y-axis direction) extending from the inlet surface to the outlet surface.

The photocatalyst filter 100 includes a plurality of first recessed portions 110 which have inlets adjacent to the inlet surface through which the unpurified air 130 is introduced and have bottoms adjacent to the outlet surface through which the purified air 140 is discharged. The unpurified air 130 is introduced into the photocatalyst filter 100 through the plurality of first recessed portions 110. The plurality of first recessed portions 110 may be regularly and/or periodically arranged. The plurality of first recessed portions 110 may be arranged parallel to each other.

The photocatalyst filter 100 includes a plurality of first surfaces 120S exposed at the inlet surface through which the unpurified air 130 is introduced. The plurality of first surfaces 120S are regularly arranged. The plurality of first surfaces 120S are disposed between the plurality of first recessed portions 110.

The plurality of first surfaces 120S are spaced apart from each other between the plurality of first recessed portions 110 spaced apart from each other along a surface of the inlet surface in one direction, for example, in an X-axis direction and/or a Z-axis direction. The plurality of first recessed portions 110 and the plurality of first surfaces 120S are alternately disposed along the surface of the inlet surface in one direction, for example, in the X-axis direction and/or the Z-axis direction. One first recessed portion 110 is surrounded by four first surfaces 120S, and one first surface 120S is surrounded by four first recessed portions 110.

Figure 14:
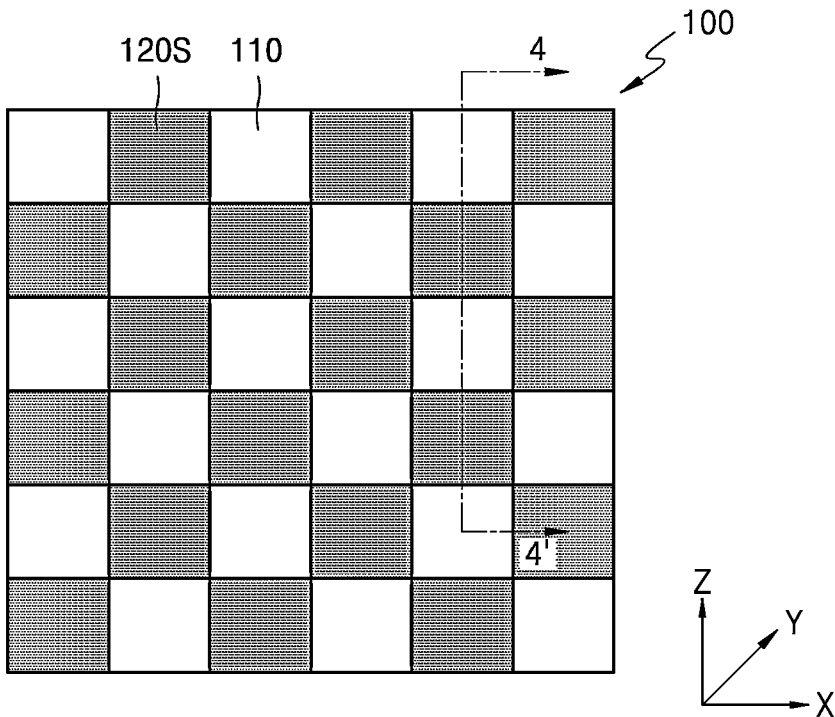
FIG. 14 is a front view of an inlet surface for unpurified air in the photocatalyst filter of FIG. 13.
Figure 15:
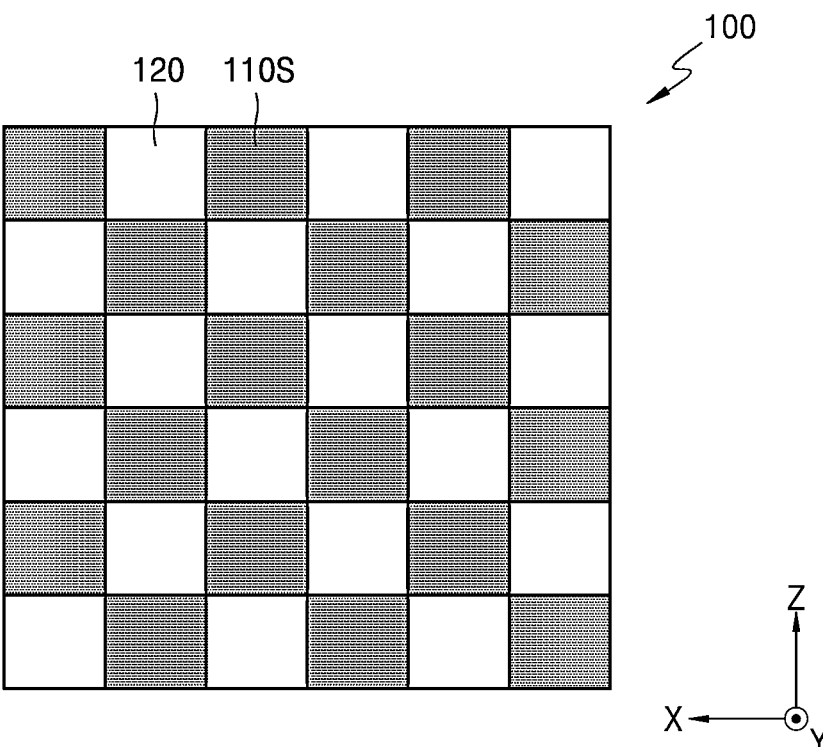
FIG. 15 is a front view of an outlet surface for purified air in the photocatalyst filter of FIG. 13.

FIG. 14 is a view of a front surface of the photocatalyst filter 100 of FIG. 13, that is, the inlet surface. FIG. 15 is a view of a rear surface of the photocatalyst filter 100 of FIG. 13, that is, the outlet surface.

Referring to FIG. 14, the inlet surface of the photocatalyst filter 100 includes the plurality of first recessed portions 110 and the plurality of first surfaces 120S.

Referring to FIG. 15, the outlet surface of the photocatalyst filter 100 includes a plurality of second recessed portions 120 and a plurality of second surfaces 110S. The plurality of second recessed portions 120 are outlets through which the purified air 140 is discharged. The purified air 140 discharged through the second recessed portion 120 may be air in which a second compound has been removed from the unpurified air 130 introduced through the first recessed portion 110 or may be a harmless gas obtained by decomposing the second compound.

The plurality of second recessed portions 120 may be regularly and/or periodically arranged. The plurality of second surfaces 110S are regularly arranged. The plurality of second surfaces 110S are disposed between the plurality of second recessed portions 120.

The plurality of second surfaces 110S correspond to the plurality of first recessed portions 110, and the plurality of second recessed portions 120 correspond to the plurality of first surfaces 120S.

Referring to FIGS. 13 and 15, the second surface 110S corresponds to a bottom of the first recessed portion 110, and the first surface 120S corresponds to a bottom of the second recessed portion 120.

Figure 16:
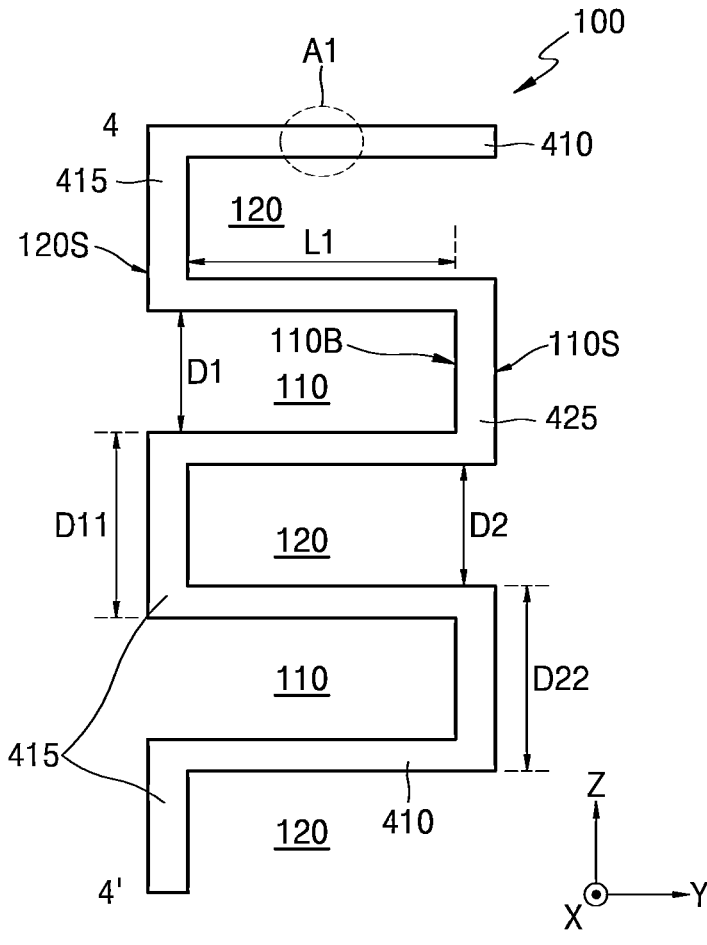
FIG. 16 is a cross-sectional view taken along line 4-4' of the photocatalyst filter of FIG. 13.

FIG. 16 is a cross-sectional view taken along line 4-4' of FIG. 14.

The photocatalyst filter 100 may have a single structure or a single frame. The photocatalyst filter 100 may have a frame of which the entirety is made of the same material, for example, a ceramic material, a polymer material, or a metal material. The photocatalyst filter 100 has, for example, a single body or monolithic structure of which the entirety is integrally formed. Alternatively, the photocatalyst filter 100 may have a multi-layered structure or a multi-layered frame. For example, although not shown in the drawings, the photocatalyst filter 100 has a multi-layered structure including a solid substrate and an organic-inorganic hybrid catalyst disposed on the solid substrate.

Referring to FIGS. 14 and 15, the photocatalyst filter 100 is a structure having a frame in which the plurality of first recessed portions 110 and the plurality of second recessed portions 120 are sequentially disposed in the Z-axis direction. The photocatalyst filter 100 includes a plurality of horizontal regions 410 and a plurality of vertical regions 415 and 425. The plurality of horizontal regions 410 are spaced apart from each other in the Z-axis direction. The Z-axis direction corresponds to a vertical direction. The plurality of horizontal regions 410 are disposed parallel to each other in the Y-axis direction. The plurality of horizontal regions 410 have the same length or different lengths. The plurality of horizontal regions 410 are disposed between the plurality of vertical regions 415 and 425. The plurality of horizontal regions 410 are physically connected to each other through the plurality of vertical regions 415 and 425. The plurality of vertical regions 415 and 425 are disposed parallel to each other and are spaced apart from each other. The plurality of vertical regions 415 and 425 are spaced apart from each other in the Z-axis direction. The Z-axis direction corresponds to the vertical direction. The plurality of vertical regions 415 and 425 are disposed parallel to each other in the Y-axis direction. The plurality of vertical regions 415 and 425 have the same length or different lengths. The plurality of vertical regions 415 and 425 are disposed between the plurality of horizontal regions 410. The plurality of vertical regions 415 and 425 are physically connected to each other through the plurality of horizontal regions 410. The plurality of vertical regions 415 and 425 include a plurality of first vertical regions 415 and a plurality of second vertical regions 425. The plurality of first vertical regions 415 and the plurality of second vertical regions 425 are spaced apart from each other in the Y-axis direction. The plurality of first vertical regions 415 are spaced apart from each other in the Z-axis direction. The plurality of second vertical regions 425 are also spaced apart from each other in the Z-axis direction. The plurality of first vertical regions 415 are disposed on the inlet surface through which the unpurified air 130 is supplied. The plurality of second vertical regions 425 are disposed on the outlet surface through which the purified air 140 is discharged.

The plurality of horizontal regions 410 correspond to walls of the first recessed portions 110 and the second recessed portions 120. Each of the plurality of horizontal regions 410 is positioned between the first recessed portion 110 and the second recessed portion 120 and becomes a boundary between the first recessed portion 110 and the second recessed portion 120. The walls correspond to sidewalls of the first recessed portion 110 and the second recessed portion 120. The plurality of horizontal regions 410 have the same thickness or different thicknesses. A thickness of the plurality of horizontal regions 410 is the same as or different from a thickness of the plurality of vertical regions 415 and 425. The horizontal regions 410 serving as the walls of the first recessed portions 110 are spaced apart from each other by a first distance D1 in the Z-axis direction. The horizontal regions 410 serving as the walls of the second recessed portions 120 are spaced apart from each other by a second distance D2 in the Z-axis direction. The first distance D1 is the same or different from the second distance D2. A diameter and/or area of an inlet of the first recessed portion 110 are the same as or different from a diameter and/or area of an inlet of the second recessed portion 120. Lengths L1 of the plurality of horizontal regions 410 in the Y-axis direction are the same as or different from each other. Depths of the first recessed portion 110 and the second recessed portion 120 are defined by the length L1 of the horizontal region 410 in the Y-axis direction. The first recessed portions 110 and the second recessed portions 120 have the same thickness or different thicknesses. The plurality of first vertical regions 415 form bottoms of the second recessed portions 120. The plurality of second vertical regions 425 form bottoms of the first recessed portions 110. Air permeability of the bottom of the first recessed portion 110 is the same as or different from air permeability of the bottom of the portion 120. A diameter D11 of the first vertical region 415 is the same as or different from a diameter D22 of the second vertical region 425. The first vertical region 415 and the second vertical region 425 have the same or different thicknesses in the Y-axis direction.

The plurality of horizontal regions 410 and the plurality of vertical regions 415 and 425 may have a single body or monolithic structure of which the entirety is integrally formed and may be made of the same material.

Figure 17:
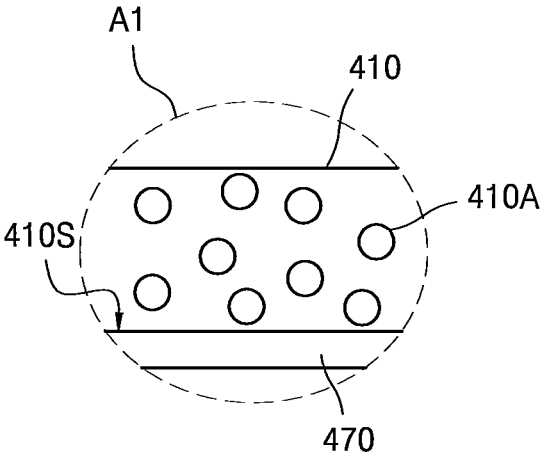
FIG. 17 is an enlarged cross-sectional view of a first portion A1 of FIG. 16.

FIG. 17 is an enlarged view of a first portion A1 of the horizontal region 410 of FIG. 16.

Referring to FIG. 17, the horizontal region 410 includes pores 410A. The vertical regions 415 and 425 include pores or do not include pores.

The horizontal region 410 and the vertical regions 415 and 425 include pores, and a pore density of the vertical regions 415 and 425 is higher or lower than a pore density of the horizontal region 410.

For example, the first vertical region 415 includes pores, and the second vertical region 425 does not include pores. Alternatively, the first vertical region 415 does not include pores, and the second vertical region 425 includes pores.

The first vertical region 415 and the second vertical region 425 include pores, and the pore density of the second vertical region 425 is higher or lower than the pore density of the first vertical region 415.

A catalyst layer 470 including the photo catalyst of an embodiment is disposed on a surface 410S of the horizontal region 410 which is to be irradiated with energy (light). For example, the catalyst layer 470 is disposed on all of the horizontal region 410 and the vertical regions 415 and 425.

An air purifier according to still another embodiment may include a photocatalyst filter including the above-described p-n heterojunction photocatalyst.

The air purifier may include a catalyst module including the above-described photocatalyst filter. The catalyst module may include the above-described photocatalyst filter and a light-emitting unit disposed to irradiate light, which is energy for activating a catalyst, onto the photocatalyst filter. The light-emitting unit may include a light source array including one or more light sources. The light-emitting unit may include a substrate, a light-emitting element provided on the substrate, and a capsule which seals and protects the light-emitting element. The light-emitting element may be a UV-light-emitting diode (LED). The substrate may include a control unit for controlling the operation of the light-emitting element, for example, a circuit unit. The capsule may be formed on the substrate and may be provided to cover the entire light-emitting element on the substrate. The capsule may be made of a material that is transparent to light emitted from the light-emitting element. The catalyst module may further include a circulation fan disposed toward an opposite surface of the photocatalyst filter on which the light-emitting unit is disposed. The light-emitting unit and the circulation fan are connected to a power source. When the catalyst module operates, the light-emitting unit emits light to a surface of the photocatalyst filter facing the light-emitting unit, and the photocatalyst filter absorbs the emitted light to form an activated photocatalyst layer on the surface. As described above with reference to FIGS. 1 and 2, the activated catalyst layer may photolyze gaseous pollutants utilizing singlet oxygen ($^1O_2$) as an ROS.

In the air purifier, a gas inlet and a gas outlet may be formed in one side surface and the other side surface parallel to the one side surface, and the above-described catalyst module may be mounted therein such that the circulation fan is positioned on a side surface on which the gas outlet is formed.

An air purifying system according to yet another embodiment may include the above-described air purifier.

The air purifying system may include a supply means which supplies air including gaseous pollutants, and an air purifying means which is equipped with the above-described catalyst module configured to decompose gaseous pollutants in the air supplied from the supply means and discharges air in which the gaseous pollutants are decomposed and removed. The air purifying system may further include an analysis means which measures a type and concentration of gaseous pollutants, for example, a VOC present in the air purifying means. Examples of the analysis means may include an IR analyzer, an optical beam spectrometer, and the like. The analysis means is connected to the air purifying means.

The supply means may include an air supply unit which includes gaseous pollutants and a control unit which detects a flow of air discharged from the air supply unit and adjusts a content thereof.

A method of preparing a p-n heterojunction photocatalyst according to yet another embodiment includes adding first compound particles to one or more second compound precursor solutions to obtain a mixture and drying the mixture to prepare a granule type composite including the first compound particles and second compound particles on at least a portion of surfaces of the first compound particles. The composite may have a size of about 1 μm to about 5 μm based on a major axis, a standard deviation of the size may be about ±0.9 μm or less, and upon exposure to energy irradiation, the composite may generate an ROS of singlet oxygen ($^1O_2$) to induce photolysis of gaseous pollutants.

Regarding the method of preparing a p-n heterojunction photocatalyst, a p-n heterojunction photocatalyst may be prepared using a one-pot synthesis method. The one-pot synthesis method may be used to increase a contact area between the first compound particles and the second compound particles, thereby facilitating an electron transfer in the composite.

The mixture is obtained by adding the first compound particles to one or more second compound precursor solutions.

For example, one or more second compound precursor solutions may be separately prepared.

In the mixture, the first compound particles may be added to one second compound precursor solution of the second compound precursor solutions to obtain a first mixture, and another second compound precursor solution may be added thereto to obtain a second mixture. Alternatively, one or more second compound precursor solutions may be mixed to obtain a mixed solution, and then the first compound particles may be added thereto to obtain the mixture.

The second compound precursor may include $Bi(NO_3)_3$, $Bi(COOCH_3)_3$, KI, $Fe(NO_3)_3$, $La(NO_3)_3$, $FeSO_4$, $La_2(CO_3)_2(OH)_2$, $Fe_2O_3$, a hydrate thereof, or a combination thereof.

The first compound particles may include $TiO_2$, $BiVO_4$, ZnO, $WO_3$, CdS, $BaTiO_3$, or a combination thereof.

The first compound particles may be secondary particles in which nano-sized primary particles are aggregated. The first compound particles may be in a crystalline phase.

A content of a second compound precursor may be in a range of about 5 wt % to about 50 wt with respect to the total weight of the composite. For example, with respect to the total weight of the composite, the content of the second compound precursor may be in a range of about 10 wt % to about 50 wt %, may be in a range of, for example, about 10 wt % to about 40 wt %, or may be in a range of, for example, about 10 wt % to about 30 wt %.

With respect to the total weight of the composite, a content of the first compound particles may be in a range of about 50 wt % to about 95 wt %, may be in a range of, for example, about 50 wt % to about 90 wt %, may be in a range of, for example, about 60 wt % to about 90 wt %, or may be in a range of, for example, about 70 wt % to about 90 wt %.

Accordingly, it is possible to provide a p-n heterojunction photocatalyst that effectively photolyzes gaseous pollutants utilizing singlet oxygen ($^1O_2$) as an ROS having a long lifetime and diffusion distance in a gas phase within a content range of the second compound precursor and the first compound particles.

The drying of the mixture may be performed for about 12 hours to 30 hours at a temperature of about 60° C. to about 100° C. under a vacuum atmosphere. For example, the drying of the mixture may be performed for about 12 hours to about 24 hours at a temperature of about 60° C. to about 80° C. under vacuum.

The method may further include, after the drying of the mixture, performing drying for 1 hour to 5 hours at a temperature of 150° C. to 250° C. under an air atmosphere. For example, after the drying of the mixture, drying may be performed for about 2 hours to about 4 hours at a temperature of about 180° C. to about 220° C. under an air atmosphere.

Hereinafter, Examples and Comparative Examples of the disclosure will be described. However, the following Examples are merely Examples of the disclosure, and the disclosure is not limited to the following Examples.

EXAMPLES

Example 1: BiOI/TiO$_2$ Composite p-n Heterojunction Photocatalyst

A BiOI/TiO$_2$ composite p-n heterojunction photocatalyst was prepared using a one-pot synthesis method as follows.

A bismuth (Bi) precursor-containing solution was prepared by dissolving 1.45 g of bismuth nitrate pentahydrate ($Bi(NO_3)_3$ $5H_2O$ (obtained from Sigma-Aldrich Co.) as a second compound precursor solution in 180 ml of a 100 mM acetic acid. solution. A first mixture was obtained by adding 9.5 g of TiO$_2$ (anatase crystal phase (obtained from Ishihara Inc., Japan) as first compound particles to the bismuth (Bi) precursor-containing solution.

Separately, a potassium iodide (KI) aqueous solution was prepared by adding 0.50 g of potassium iodide (KI) (obtained from Sigma-Aldrich Co.) as a second compound precursor solution to 30 mL of distilled water. The first mixture and the potassium iodide (KI) aqueous solution were each stirred at a revolution speed of 500 rpm for 30 minutes and sonicated for 30 minutes, and then the potassium iodide (KI) aqueous solution was slowly added dropwise to the first mixture through continuous magnetic stirring to obtain a second mixture.

The second mixture was stirred for 2 hours and then centrifuged to obtain a granule type composite powder. The composite powder was washed using deionized water and dried overnight at a temperature of 80° C. under vacuum. In order to remove the remaining carbon on the composite a muffle furnace was used, the dried composite powder was heat-treated for 3 hours at a temperature of 200° C. at a heating ramp rate of 5° C./min under an air atmosphere, to provide a BiOI/TiO$_2$ composite p-n heterojunction photocatalyst. In a BiOI/TiO$_2$ composite, a content of BiOI particles was 10 wt % based on the total weight of the BiOI/TiO$_2$ composite.

Example 2: BiOI/TiO$_2$ Composite p-n Heterojunction Photocatalyst

A BiOI/TiO$_2$ composite p-n heterojunction photocatalyst was prepared in the same manner as in Example 1, except that bismuth nitrate pentahydrate ($Bi(NO_3)_3$ $5H_2O$ and potassium iodide (KI) were used such that, in a BiOI/TiO$_2$ composite, a content of BiOI particles was 5 wt % based on the total weight of the BiOI/TiO$_2$ composite.

Example 3: BiOI/TiO$_2$ Composite p-n Heterojunction Photocatalyst

A BiOI/TiO$_2$ composite p-n heterojunction photocatalyst was prepared in the same manner as in Example 1, except that bismuth nitrate pentahydrate ($Bi(NO_3)_3$ $5H_2O$ and potassium iodide (KI) were used such that, in a BiOI/TiO$_2$ composite, a content of BiOI particles was 30 wt % based on the total weight of the BiOI/TiO$_2$ composite.

Example 4: BiOI/TiO$_2$ Composite p-n Heterojunction Photocatalyst

A BiOI/TiO$_2$ composite p-n heterojunction photocatalyst was prepared in the same manner as in Example 1, except that bismuth nitrate pentahydrate (Bi(NO$_3$)$_3$ 5H$_2$O and potassium iodide (KI) were used such that, in a BiOI/TiO$_2$ composite, a content of BiOI particles was 50 wt % based on the total weight of the BiOI/TiO$_2$ composite.

Comparative Example 1: TiO$_2$ Photocatalyst

A TiO$_2$ photocatalyst having an anatase crystal phase (obtained from Ishihara Inc., in Japan) was used.

Comparative Example 2: BiOI Photocatalyst

A bismuth (Bi) precursor-containing solution was prepared by dissolving 1.45 g of bismuth nitrate pentahydrate (Bi(NO$_3$)$_3$ 5H$_2$O in 180 ml of a 100 mM acetic acid solution. Separately, a potassium iodide (KI) aqueous solution was prepared by adding 0.50 g of potassium iodide (KI) to 30 mL of distilled water. The bismuth (Bi) precursor-containing solution and the potassium iodide (KI) aqueous solution were mixed and stirred at a revolution speed of 500 rpm for 30 minutes to obtain a mixture. The mixture was washed using deionized water and dried at a temperature of 80° C. for 12 hours under vacuum to provide a BiOI photocatalyst in a powder form.

Comparative Example 3: BiOI/TiO2 Composite Photocatalyst 96 mL of ethylene glycol was put into a high-temperature/high-pressure reactor (capacity: 120 mL) made of stainless steel, 0.58 g of potassium iodide (KI) and 1.7 g of bismuth nitrate (Bi(NO$_3$)$_3$) were sequentially dissolved in the ethylene glycol. The high-temperature/high-pressure reactor was sealed and put into a high-temperature furnace and heated at a temperature of 160° C. for 12 hours. The high-temperature and high-pressure reactor was cooled to room temperature and then opened. The contents were washed several times with water and ethanol. The solid was separated with a centrifuge and dried at a temperature of 80° C. for 12 hours to provide a BiOI photocatalyst in a powder form. A TiO$_2$ powder (particle diameter: 10 nm), a commercial photocatalyst (obtained from Ishihara Inc., in Japan) was used. 0.1 g of collected BiOI and 0.9 g of the TiO$_2$ were added to a 250 mL round-bottom flask, 10 mL of distilled water was added to the flask and mixed well. The water was completely removed using a rotary evaporator to provide a BiOI/TiO$_2$ composite photocatalyst. A weight ratio of BiOI to TiO$_2$ in a BiOI/TiO2 composite was 10 wt %:90 wt %.

Analysis Example 1: SEM and TEM-Fast Fourier Transform (FFT) Analysis-Morphology, Size Analysis Surfaces of the TiO$_2$ photocatalyst of Comparative Example 1, the BiOI photocatalyst of Comparative Example 2, the BiOI/TiO$_2$ composite photocatalyst of Comparative Example 3, and the BiOI/TiO$_2$ composite p-n heterojunction photocatalyst of Example 1 were analyzed using a SEM (SU-8030 manufactured by Hitachi, Ltd.) and a TEM (Titan G2 manufactured by FEI Company, TEM-FFT). The results (micrographs) are shown in FIGS. 3A to 3E, respectively.

Figure 3A:
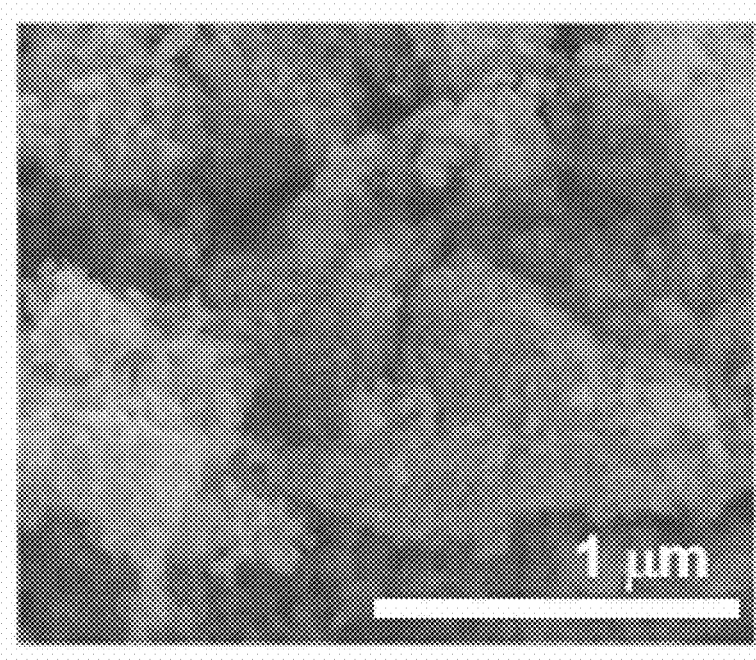
FIG. 3A is a scanning electron microscope image of a $TiO_2$ photocatalyst of Comparative Example 1 (scale bar: 1 μm).

Referring to FIG. 3A, FIG. 3A shows that the TiO$_2$ photocatalyst of Comparative Example 1 includes substantially uniform particles having a size of about 20 nm to about 30 nm.

Figure 3B:
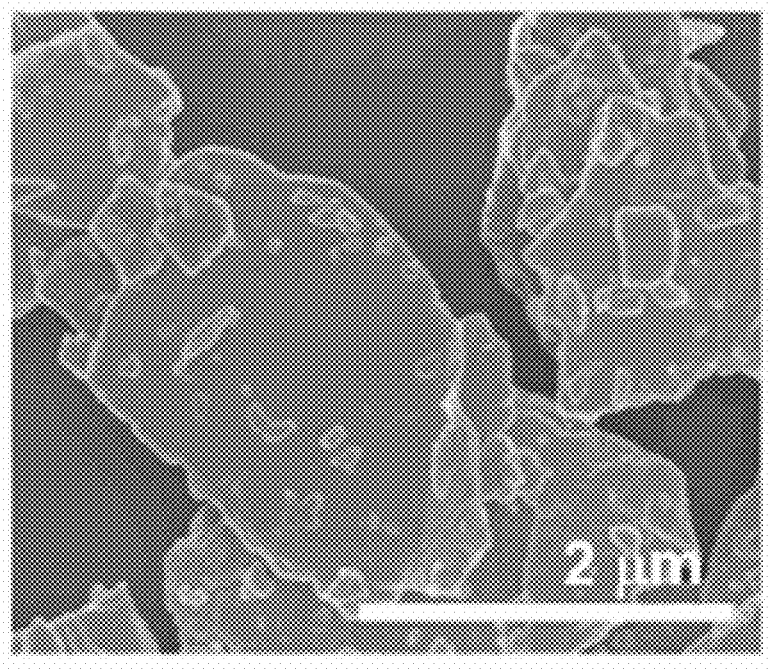
FIGS. 3B and 3C are scanning electron microscope images of a BiOI photocatalyst of Comparative Example 2, and a BiOI/$TiO_2$ composite photocatalyst of Comparative Example 3, (scale bar: 2 μm), respectively.

Referring to FIG. 3B, FIG. 3B shows that the BiOI photocatalyst prepared in Comparative Example 2 includes nano- or micro-sized particles.

Figure 3C:
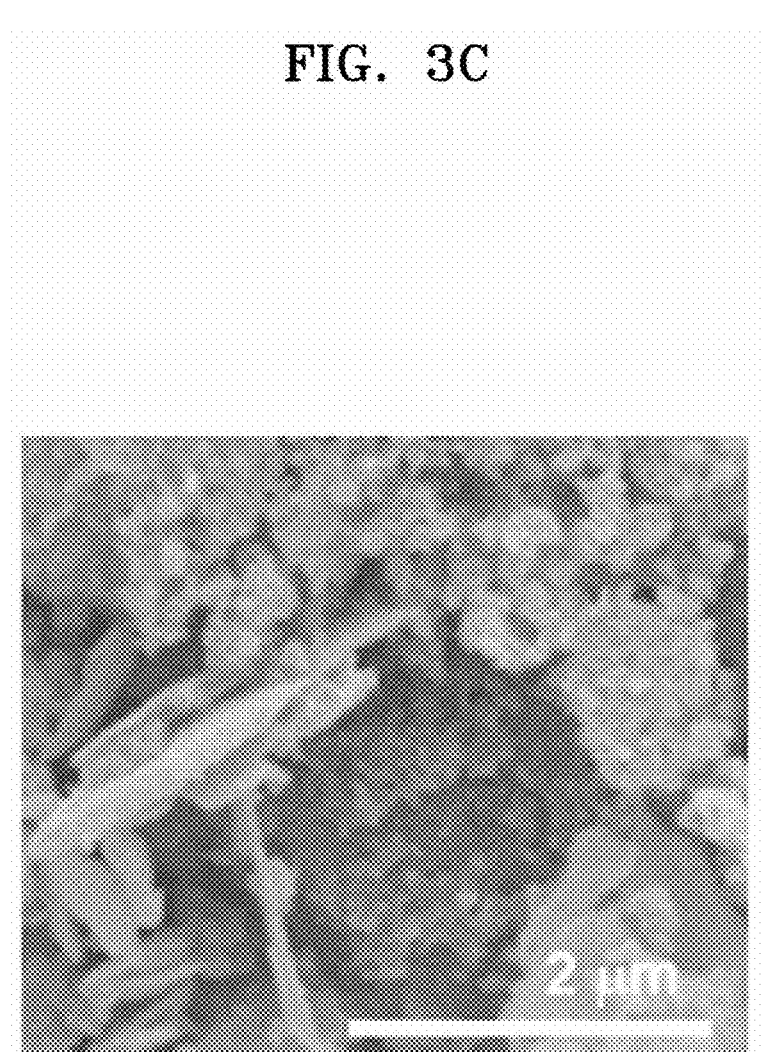
Figure 3D:
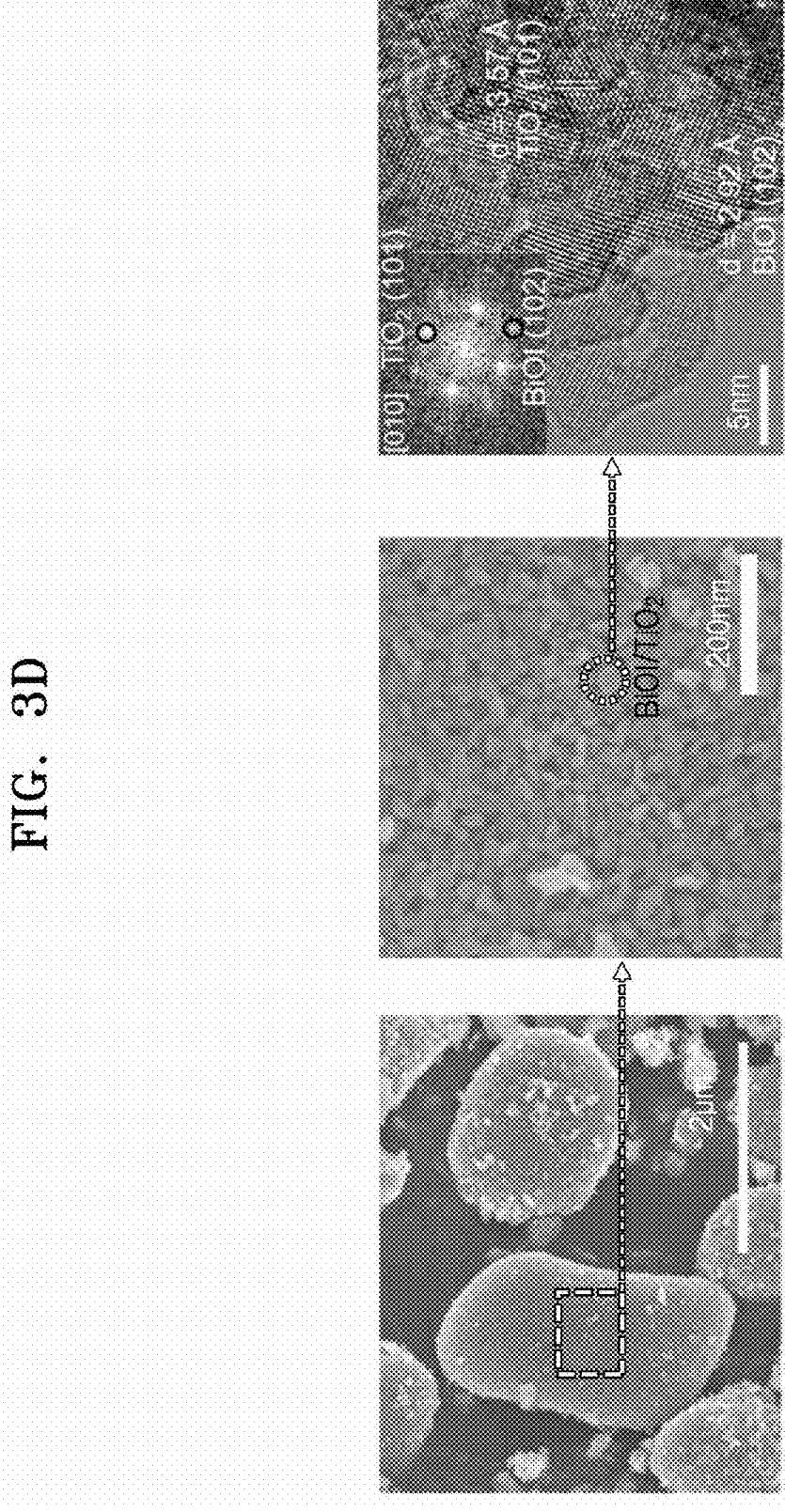
FIG. 3D are scanning electron microscope images of a BiOI/$TiO_2$ composite p-n heterojunction photocatalyst of Example 1, SEM (scale bar: 2 μm, 200 nm), and transmission electron microscope image (TEM)-fast fourier transform (FFT) (scale bar: 5 nm)

Referring to FIG. 3C, in the BiOI/TiO$_2$ composite photocatalyst prepared in Comparative Example 3, the TiO$_2$ particles do not form a composite and the BiOI and TiO$_2$ particles are shown to be spaced apart from the other, e.g., as in a simple mixture Referring to FIG. 3D, FIG. 3D shows that the BiOI/TiO$_2$ composite p-n heterojunction photocatalyst prepared in Example 1 includes a composite in which sub-nano-sized BiOI primary particles are positioned on surfaces of TiO$_2$ secondary particles which have a size of about 2 μm and in which primary particles having a size of about 20 nm to 30 nm based on a major axis are aggregated. In addition, FIG. 3D shows that, in the BiOI/TiO$_2$ composite p-n heterojunction photocatalyst prepared in Example 1, the sub-nano-sized BiOI primary particles are bound to a portion of the surfaces of the TiO$_2$ secondary particles.

Figure 3E:
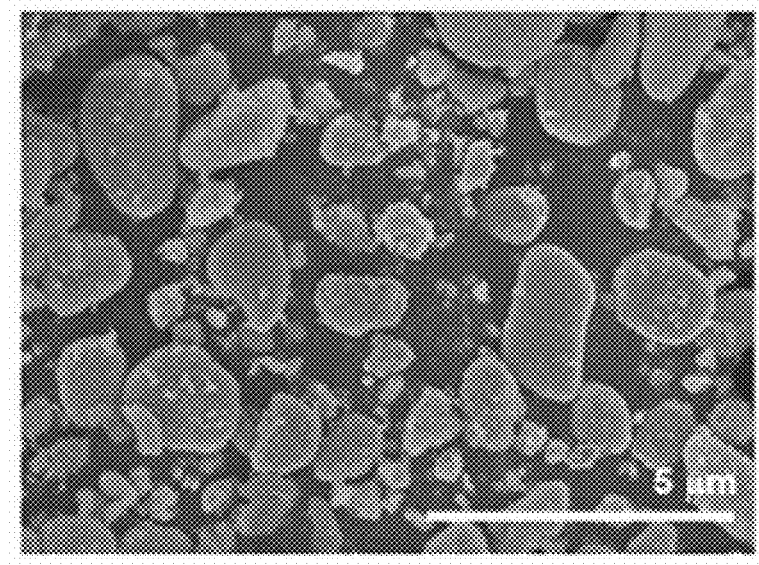
FIG. 3E is a scanning electron microscope image of a surface of the BiOI/$TiO_2$ composite p-n heterojunction photocatalyst of Example 1, (scale bar: 5 μm)

Referring to FIG. 3E, FIG. 3E shows that the BiOI/TiO$_2$ composite p-n heterojunction photocatalyst prepared in Example 1 includes a granule type composite having various shapes such as an elliptical shape, a round shape, a flake shape, a flower shape, and a rod shape.

It may be confirmed that the BiOI/TiO$_2$ composite p-n heterojunction photocatalyst prepared in Example 1 of FIGS. 3D and 3E has many contact surfaces between BiOI particles and TiO$_2$ particles as compared to the BiOI/TiO$_2$ composite photocatalyst of Comparative Example 3 of FIG. 3C. Therefore, one may expect more electronic interactions to occur in the BiOI/TiO$_2$ composite p-n heterojunction photocatalyst of Example 1.

In addition, a size of the BiOI/TiO$_2$ composite p-n heterojunction photocatalyst of Example 1 was analyzed by SEM (SU-8030 manufactured by Hitachi, Ltd.) and TEM (Titan G2 manufactured by FEI Company, TEM-FFT). The micrographs are shown in FIG. 3F.

Figure 3F:
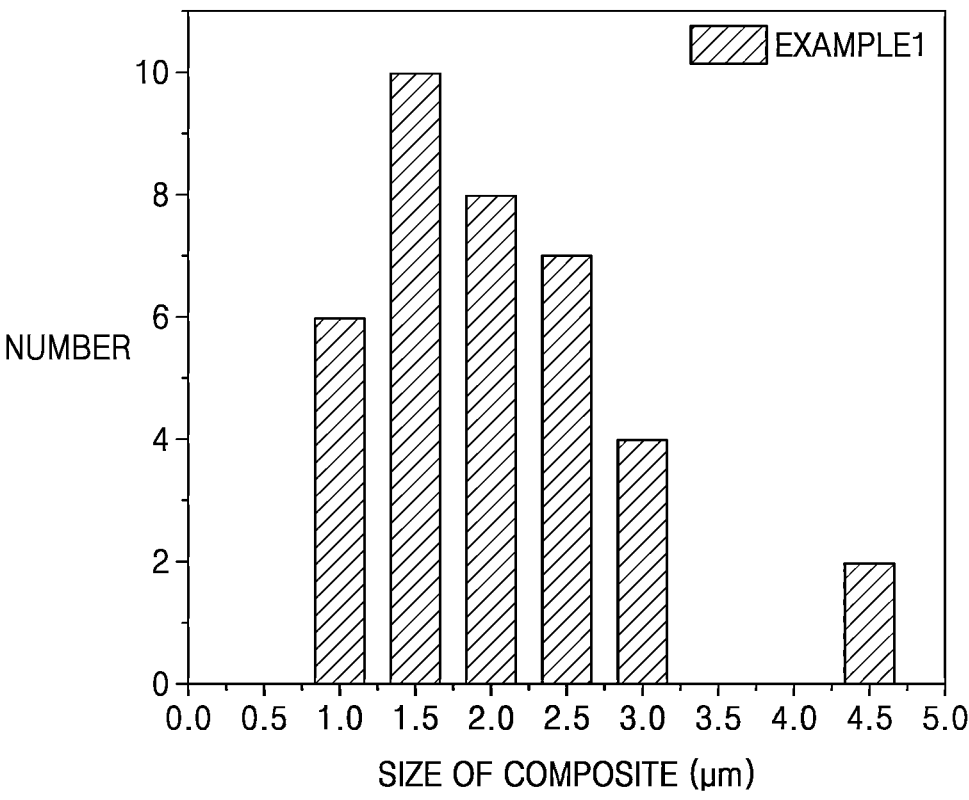
FIG. 3F is a bar chart representing a size distribution of the BiOI/$TiO_2$ composite p-n heterojunction photocatalyst of Example 1.

Referring to FIG. 3F, the size of the BiOI/TiO$_2$ composite p-n heterojunction photocatalyst of Example 1 was a minimum of 0.95 μm and a maximum of 4.66 μm based on a major axis, and a standard deviation thereof was ±0.85 μm. An average size of the BiOI/TiO$_2$ composite p-n heterojunction photocatalyst prepared in Example 1 was 2.01±0.13 μm based on the major axis.

Analysis Example 2: X-Ray Diffraction (XRD) and Scanning Transmission Electron Microscopy (STEM)-Energy Dispersive Spectroscopy (EDS) Analysis-Composite Composition Analysis The TiO$_2$ photocatalyst of Comparative Example 1, the BiOI photocatalyst of Comparative Example 2, the BiOI/TiO$_2$ composite photocatalyst of Comparative Example 3, and the BiOI/TiO$_2$ composite p-n heterojunction photocatalyst of Example 1 were subjected to an XRD analysis. The BiOI/TiO$_2$ composite p-n heterojunction photocatalyst of Example 1 was also subjected to a STEM EDS analysis. The results are shown in FIGS. 4 and 5, respectively.

Figure 4:
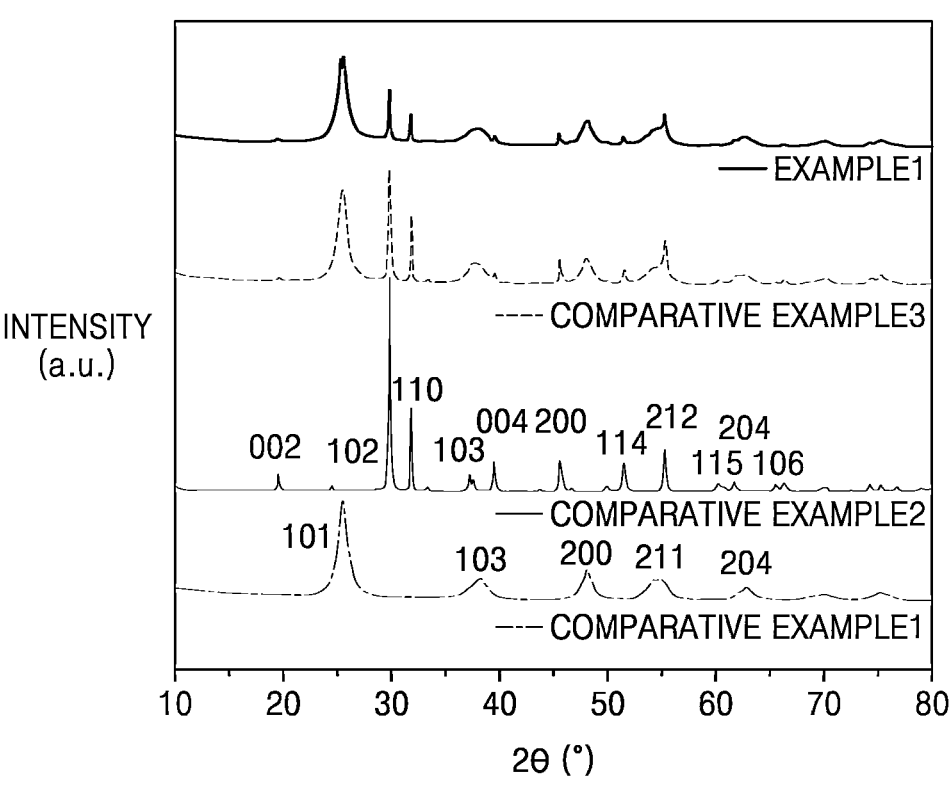
FIG. 4 are X-ray diffraction (XRD) spectra of a $TiO_2$ photocatalyst of Comparative Example 1, the BiOI photocatalyst of Comparative Example 2, the BiOI/$TiO_2$ composite photocatalyst of Comparative Example 3, and the BiOI/$TiO_2$ composite p-n heterojunction photocatalyst of Example 1.

Referring to FIG. 4, FIG. 4 indicates that the BiOI/TiO$_2$ composite p-n heterojunction photocatalyst of Example 1 is a composite photocatalyst, e.g., of $TiO_2$ of Comparative Example 1 and BiOI of Comparative Example 2.

Figure 5:
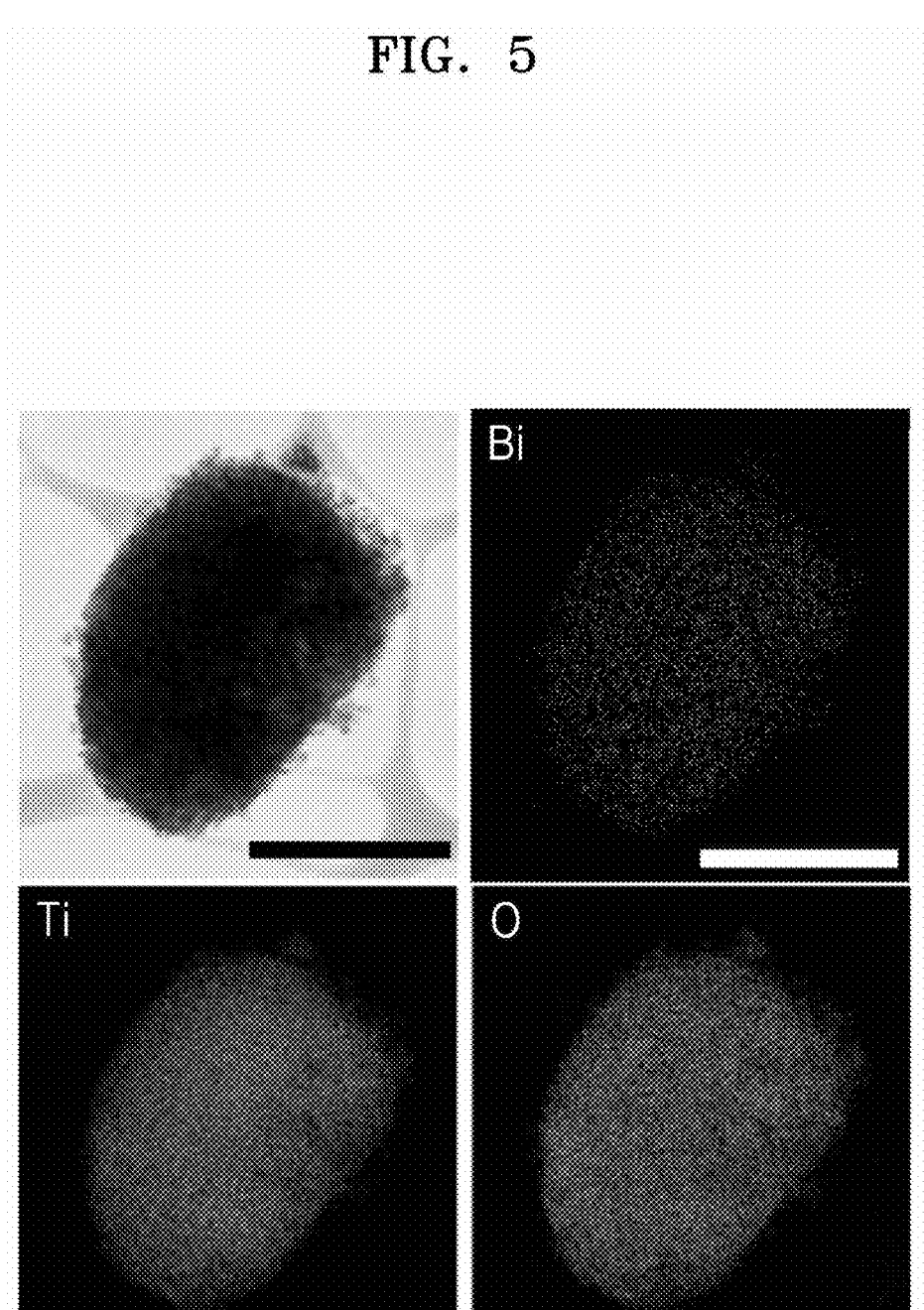
FIG. 5 shows a scanning transmission electron microscopy (STEM)-energy dispersive spectroscopy (EDS) analysis on the $BiOI/TiO_2$ composite p-n heterojunction photocatalyst of Example 1.

Referring to FIG. 5, FIG. 5 shows that the $BiOI/TiO_2$ composite p-n heterojunction photocatalyst of Example 1 is a composite photocatalyst made of $TiO_2$ of Comparative Example 1 and BiOI of Comparative Example 2, and in such a composite, a bismuth (Bi) element, a titanium (Ti) element, and an oxygen (O) element are uniformly distributed.

Analysis Example 3: XPS Analysis-Analysis of Chemical States of Composite Elements By using Quantum 2000 (manufactured by Physical Electronics, inc.), an XPS analysis was performed on chemical states of a titanium (Ti) element, a bismuth (Bi) element, an iodine (I) element, and an oxygen (O) element of the $TiO_2$ photocatalyst of Comparative Example 1, the BiOI photocatalyst of Comparative Example 2, the $BiOI/TiO_2$ composite photocatalyst of Comparative Example 3, and the $BiOI/TiO_2$ composite p-n heterojunction photocatalyst of Example 1. The XPS results are shown in FIGS. 6A to 6D, respectively.

Referring to FIGS. 6A to 6D, it is confirmed from peaks of a titanium (Ti) element, a bismuth (Bi) element, an iodine (I) element, and an oxygen (O) element that the $BiOI/TiO_2$ composite p-n heterojunction photocatalyst of Example 1 is a composite photocatalyst made of $TiO_2$ of Comparative Example 1 and BiOI of Example 2.

Figure 6A:
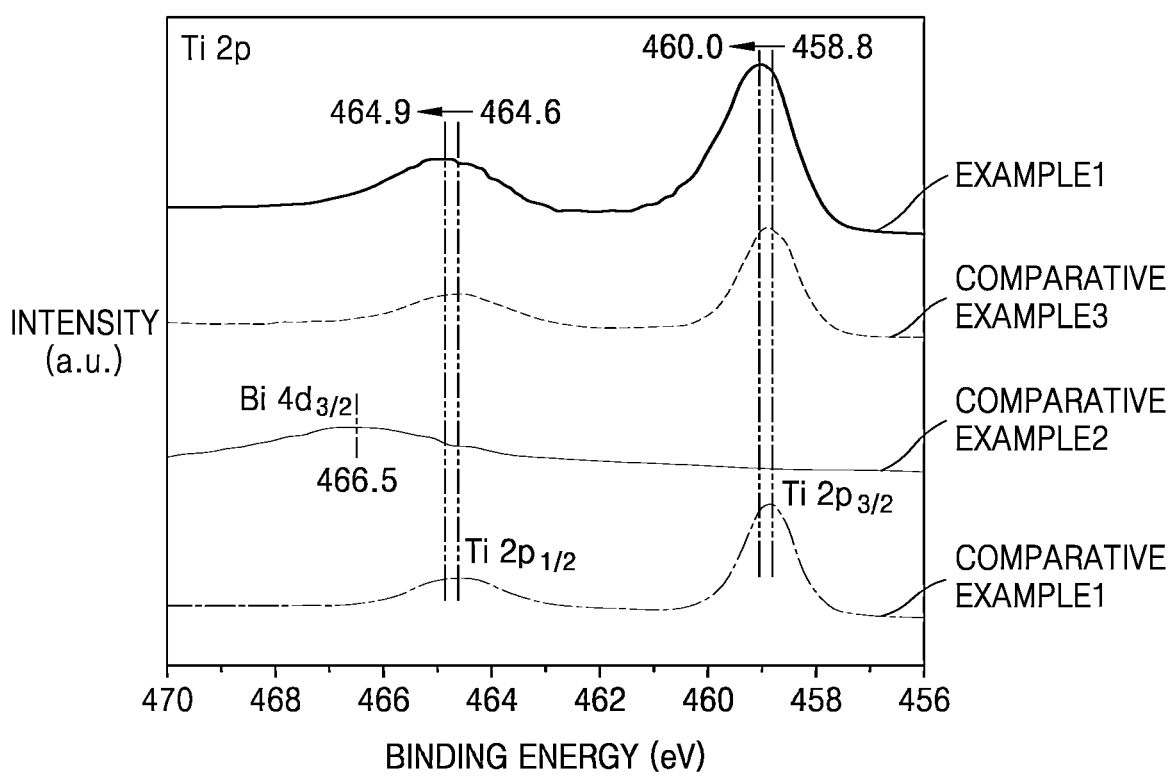
FIGS. 6A to 6D show X-ray photoemission spectroscopy (XPS) analysis on chemical states of a titanium (Ti) element, a bismuth (Bi) element, an iodine (I) element, and an oxygen (O) element of the $TiO_2$ photocatalyst of Comparative Example 1, the BiOI photocatalyst prepared in Comparative Example 2, the $BiOI/TiO_2$ composite photocatalyst prepared in Comparative Example 3, and the $BiOI/TiO_2$ composite p-n heterojunction photocatalyst prepared in Example 1, respectively.

Referring to FIG. 6A, a peak of Ti2p binding energy peak of the $BiOI/TiO_2$ composite p-n heterojunction photocatalyst of Example 1 is shifted in a positive direction with respect to a peak of Ti2p binding energy peak of the $TiO_2$ photocatalyst of Comparative Example 1.

Figure 6B:
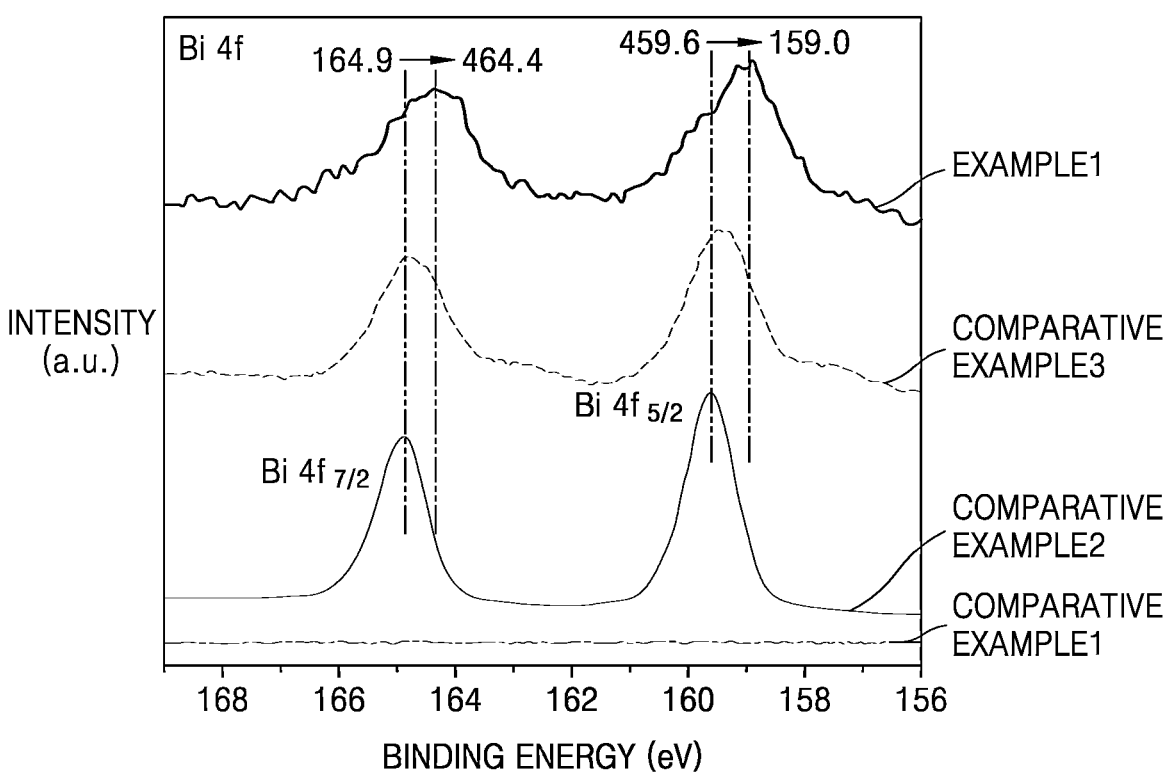
Figure 6C:
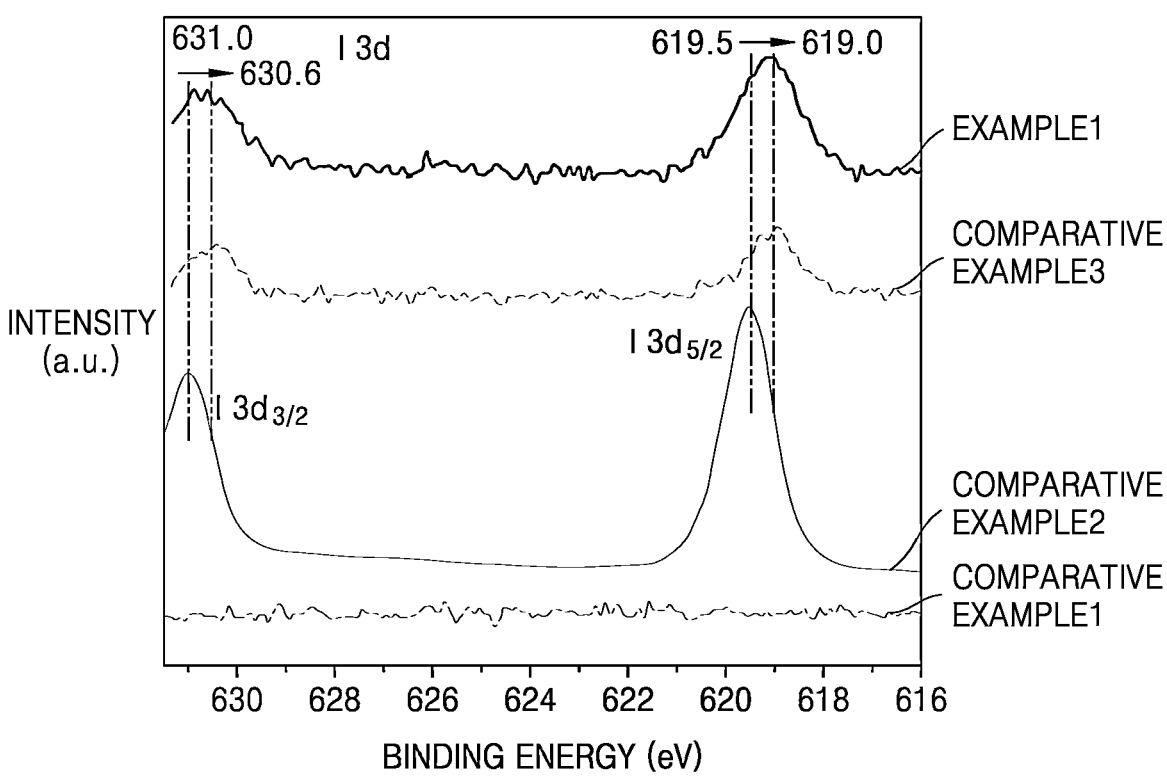

Referring to FIGS. 6B and 6C, peaks of Bi4f and 13d binding energies of the $TiO_2$ photocatalyst of Comparative Example 1 and the BiOI photocatalyst of Comparative Example 2 are respectively shifted in a negative direction with respect to peaks of Bi4f and I3d binding energies of the $TiO_2$ photocatalyst of Comparative Example 1.

The XPS data is consistent with the titanium (Ti) element having an electronegativity that is lower than electronegativity of a bismuth (Bi) element and an iodine (I) element.

Thus, it may be confirmed that, in the $BiOI/TiO_2$ composite p-n heterojunction photocatalyst prepared in Example 1, electrons may be transferred in the composite. In addition, it may be confirmed that each shift in Example 1 has a larger value as compared with Comparative Example 3. Therefore, one would expect more electrons to be transferred in the $BiOI/TiO_2$ composite p-n heterojunction photocatalyst of Example 1.

Figure 6D:
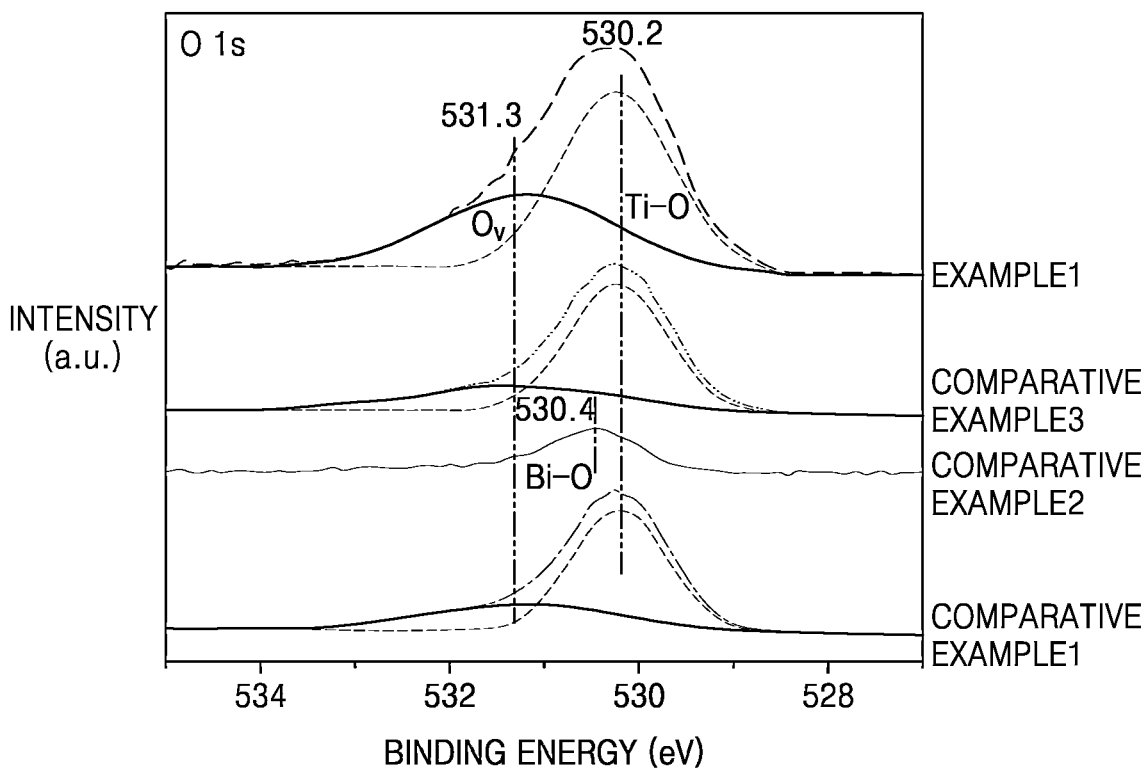

Referring to FIG. 6D, an oxygen vacancy peak of the $BiOI/TiO_2$ composite p-n heterojunction photocatalyst of Example 1 is higher than that of the $BiOI/TiO_2$ composite photocatalyst of Comparative Example 3. The XPS data is consistent with the $BiOI/TiO_2$ composite p-n heterojunction photocatalyst of Example 1 having many contact surfaces between the BiOI particles and the $TiO_2$ particles. Therefore, one would expect more electrons to be transferred inside the $BiOI/TiO_2$ composite p-n heterojunction photocatalyst of Example 1.

Figure 7A:
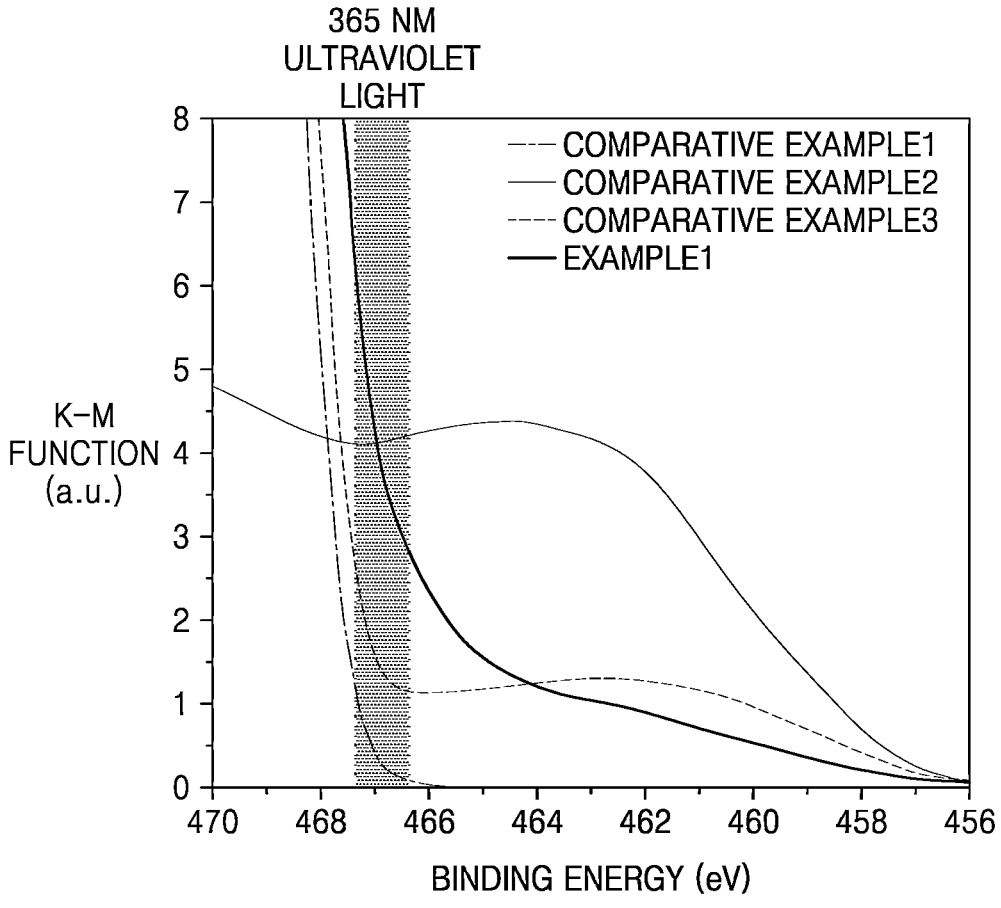
FIG. 7A shows ultraviolet (UV)-visible spectra of the $TiO_2$ photocatalyst of Comparative Example 1, the BiOI photocatalyst of Comparative Example 2, the $BiOI/TiO_2$ composite photocatalyst of Comparative Example 3, and the $BiOI/TiO_2$ composite p-n heterojunction photocatalyst of Example 1.
Figure 7B:
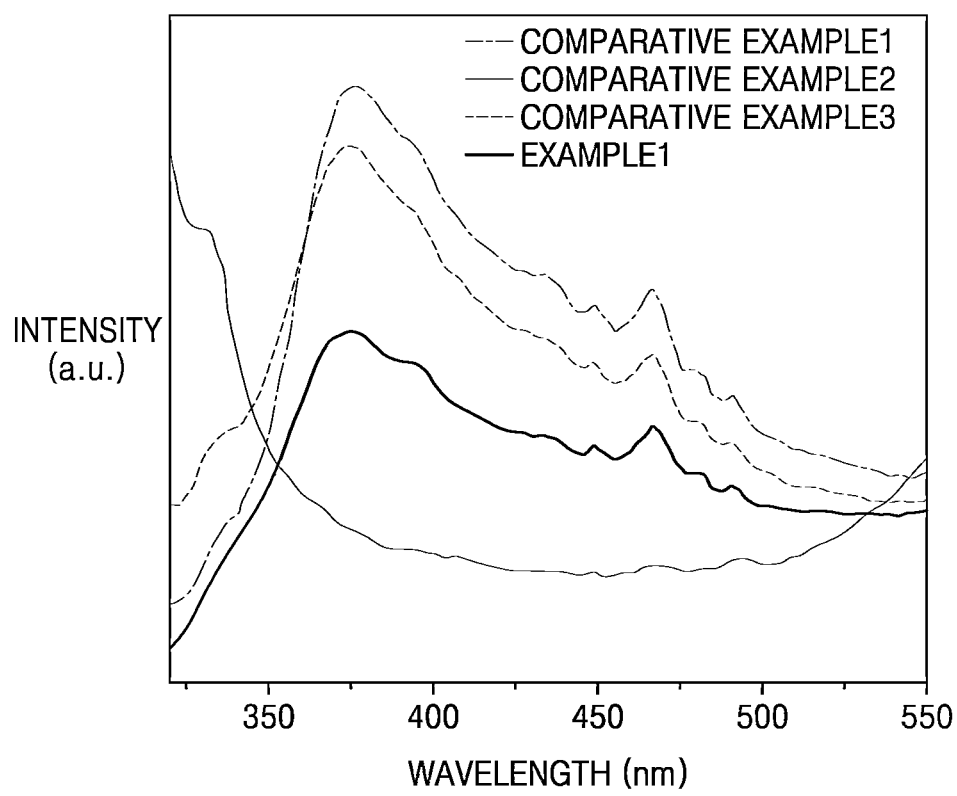
FIG. 7B shows a photoluminescence spectra of the $TiO_2$ photocatalyst of Comparative Example 1, the BiOI photocatalyst prepared in Comparative Example 2, the $BiOI/TiO_2$ composite photocatalyst prepared in Comparative Example 3, and the $BiOI/TiO_2$ composite p-n heterojunction photocatalyst of Example 1.

Analysis Example 4: UV-Visible Spectrum and Photoluminescence (PL) Spectrum Analysis An analysis was performed from a UV-visible spectrum and a PL spectrum of the $TiO_2$ photocatalyst of Comparative Example 1, the BiOI photocatalyst of Comparative Example 2, the $BiOI/TiO_2$ composite photocatalyst of Comparative Example 3, and the $BiOI/TiO_2$ composite p-n heterojunction photocatalyst of Example 1. The results are shown in FIGS. 7A and 7B, respectively. The UV-visible spectrum was recorded using a UV-visible spectrophotometer (Solidspec-3700 manufactured by Shimadzu Corporation) equipped with a diffuse reflection attachment, and from the UV-visible spectrum, the absorbance for each wavelength was substituted into a Kubelka-Munk equation and graphed. The PL spectrum was obtained using a PL instrument (Fluromax manufactured by Horiba Instruments, Inc.).

Referring to FIG. 7A, FIG. 7A shows that the $BiOI/TiO_2$ composite p-n heterojunction photocatalyst prepared in Example 1 exhibits high absorbance at a wavelength of 360 nm compared to the $TiO_2$ photocatalyst of Comparative Example 1, the BiOI photocatalyst of Comparative Example 2, and the $BiOI/TiO_2$ composite photocatalyst of Comparative Example 3.

Referring to FIG. 7B, PL of the $BiOI/TiO_2$ composite p-n heterojunction photocatalyst of Example 1 is reduced. The UV-visible and PL data is consistent with a reduced recombination of electron charges and hole charges that are separated due to an electron transfer at a p-n heterojunction. Thus, the data is consistent with electrons and holes generated by light are used for an electron transfer in the composite.

Evaluation Example 1: Impedance Evaluation

Impedance of the $TiO_2$ photocatalyst of Comparative Example 1, the $BiOI/TiO_2$ composite photocatalyst of Comparative Example 3, and the $BiOI/TiO_2$ composite p-n heterojunction photocatalyst of Example 1 was measured according to a 2-probe method using a potentiostat (WMPG 1000 manufactured by Wonatech). A frequency ranged from 0.1 MHz to 0.1 Hz. A Nyquist plot obtained from the measurement of the impedance is shown in FIG. 8.

Figure 8:
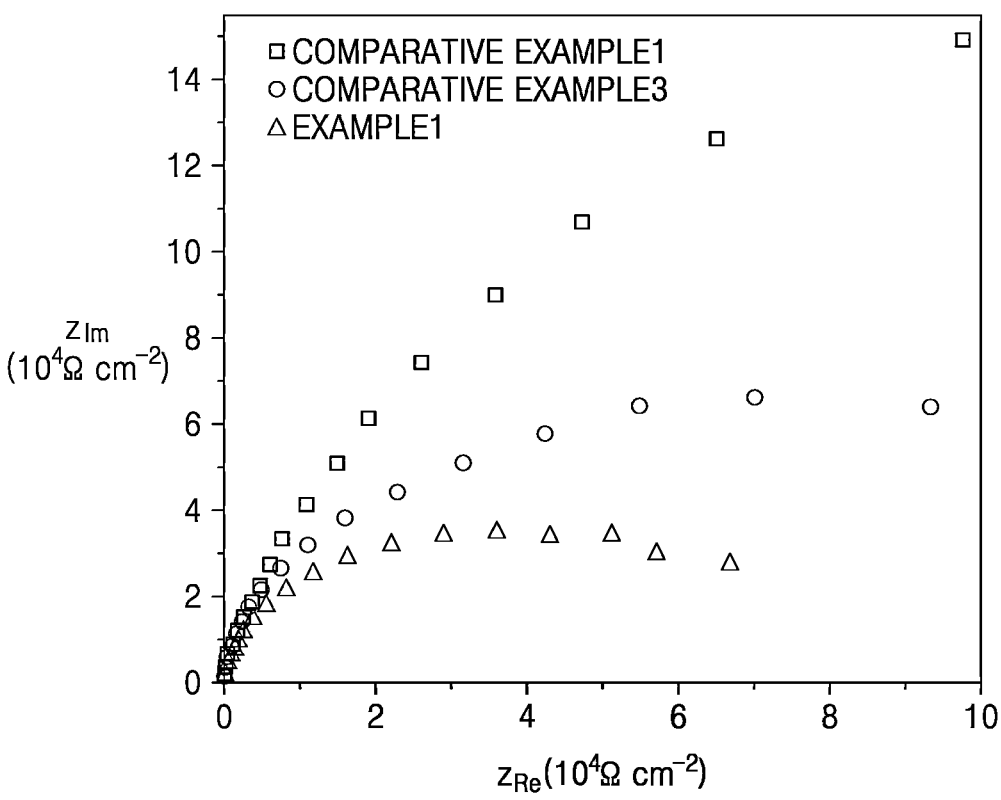
FIG. 8 shows a Niquist plot obtained by measuring impedance of the $TiO_2$ photocatalyst of Comparative Example 1, the $BiOI/TiO_2$ composite photocatalyst prepared in Comparative Example 3, and the $BiOI/TiO_2$ composite p-n heterojunction photocatalyst of Example 1.

Referring to FIG. 8, that the data is consistent with the $BiOI/TiO_2$ composite p-n heterojunction photocatalyst of Example 1 having low internal resistance compared to the $TiO_2$ photocatalyst of Comparative Example 1 and the $BiOI/TiO_2$ composite photocatalyst of Comparative Example 3.

Accordingly, the $BiOI/TiO_2$ composite p-n heterojunction photocatalyst of Example 1 has a high electron transfer at a p-n junction inducing electron-hole charge separation in the composite.

Evaluation Example 2: Evaluation of Photocurrent Density

A photocurrent density of the $TiO_2$ photocatalyst of Comparative Example 1, the BiOI photocatalyst of Comparative Example 2, the $BiOI/TiO_2$ composite photocatalyst of Comparative Example 3, and the $BiOI/TiO_2$ composite p-n heterojunction photocatalyst of Example 1 was evaluated in the following manner. The results are shown in FIG. 9.

The photocurrent density was recorded in a single cell section in a three-electrode configuration (Ag/AgCl in 3 M NaCl as a reference electrode and a Pt wire as a counter electrode).

In order to prepare an electrode, 20 μl of the photocatalyst of each Comparative Example and Example in 1 mg/ml of ethanol was drop-cast on a washed fluorine-doped tin oxide (FTO) glass electrode and completely dried at a temperature of 80° C. For an experiment, a 0.1 M phosphate buffer solution (pH 7) was used. By using a 365 nm wavelength LED lamp (manufactured by Fiber Optics Korea Co., Ltd.), UV light was irradiated at an intensity of 50 mW/cm$^2$ and a potential of 0.5 V vs Ag/AgCl between 0 seconds and 100 seconds (light), and UV irradiation was stopped between 100 seconds and 140 seconds (dark) to measure the photo-current density.

Figure 9:
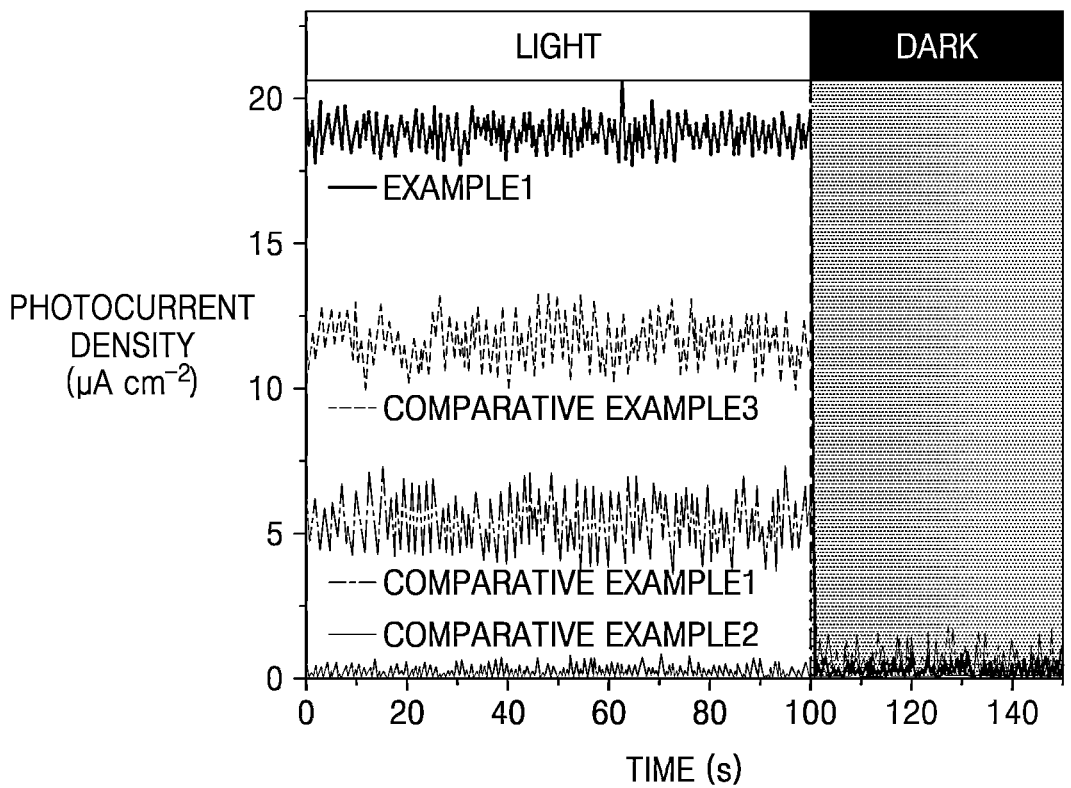
FIG. 9 shows a result of measuring a photocurrent density of the $TiO_2$ photocatalyst of Comparative Example 1, the BiOI photocatalyst prepared in Comparative Example 2, the $BiOI/TiO_2$ composite photocatalyst of Comparative Example 3, and the $BiOI/TiO_2$ composite p-n heterojunction photocatalyst of Example 1.

Referring to FIG. 9, the photocurrent density of the BiOI/TiO$_2$ composite p-n heterojunction photocatalyst of Example 1 is greater than the photocurrent density of the TiO$_2$ photocatalyst of Comparative Example 1, the BiOI photocatalyst of Comparative Example 2, and the BiOI/TiO$_2$ photocatalyst of Comparative Example 3. Thus, the data is consistent with the BiOI/TiO$_2$ composite p-n heterojunction photocatalyst of Example 1 having good (acceptable) electron transfer with little or no electron-hole recombination in the composite.

Evaluation Example 3: PL and Electron Paramagnetic Resonance (EPR) Spectrum Evaluation-ROS Analysis To analyze an ROS, a PL spectrum and an EPR spectrum experiments were conducted for the TiO$_2$ photocatalyst of Comparative Example 1, the BiOI photocatalyst of Comparative Example 2, the BiOI/TiO$_2$ composite photocatalyst of Comparative Example 3, and the BiOI/TiO$_2$ composite p-n heterojunction photocatalyst of Example 1. The results are shown in FIGS. 10, 11A, and 11B.

For the EPR experiment, a JES-FA 200 JEOL instrument was used, and 5,5-dimethyl-1-pyrroline-N-oxide (DMPO) and 2,2,6,6-tetramethylpiperidine (TEMP) were used as a spin-trapping agent. The photocatalyst of each Comparative Example and Example was dispersed at a concentration of 2 mg/ml (5 mg) in the spin trapping solution. A concentration of the spin trapping solution was 350 mM in the case of DMPO and was 240 mM in the case of TEMP. In the case of —O$_2^-$ trapping, methanol was added to the spin trapping solution to avoid interference of ·OH. The spin trapping solution was irradiated with 365 nm UV light for 10 minutes, and the resulting suspension was filtered through a 0.22 µm micron syringe filter. All spectra were obtained at a resonance frequency of 9.64 GHz, a microwave power of 3 mW, a modulation amplitude of 1.0 G, and a modulation frequency of 100 kHz. During HCHO decomposition, in order to identify an intermediate radical, 37 wt % of a formaldehyde solution (obtained from Sigma-Aldrich Co.) was additionally added to the spin trapping solution (9:1 v/v).

Figure 10:
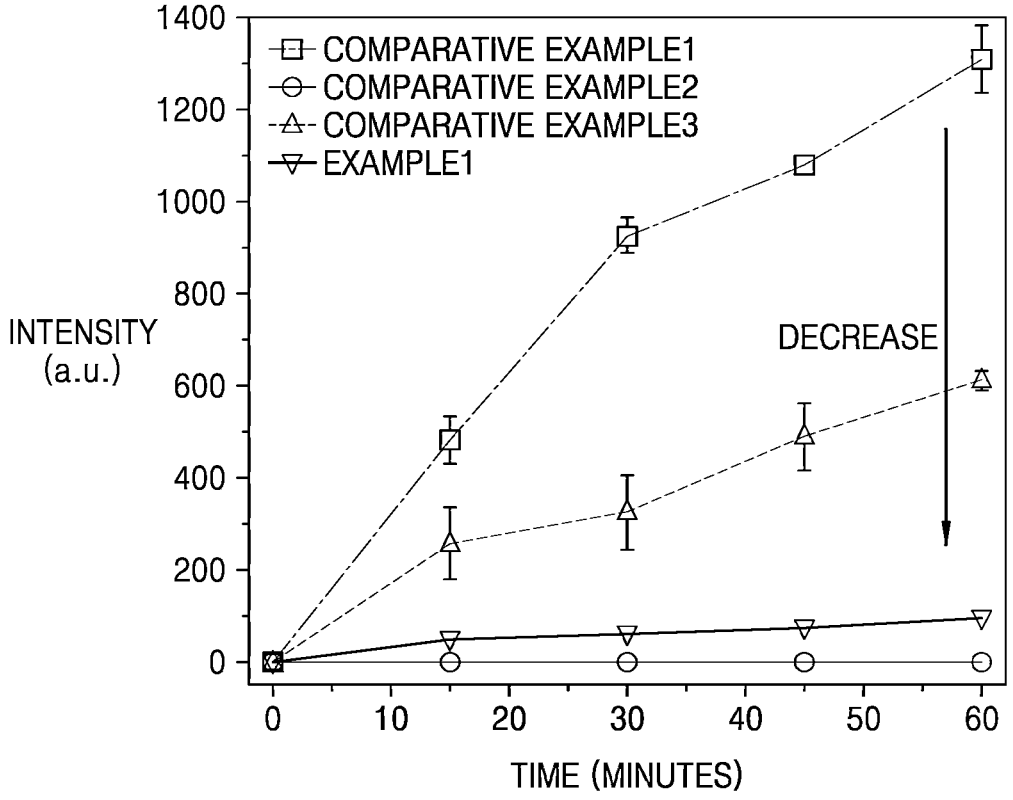
FIG. 10 is a plot of photoluminescence data obtained by measuring intensity over time indicating hydroxyl radical ($\cdot$OH) generation, for the $TiO_2$ photocatalyst of Comparative Example 1, the BiOI photocatalyst of Comparative Example 2, the $BiOI/TiO_2$ composite photocatalyst of Comparative Example 3, and the $BiOI/TiO_2$ composite p-n heterojunction photocatalyst of Example 1.
Figure 11A:
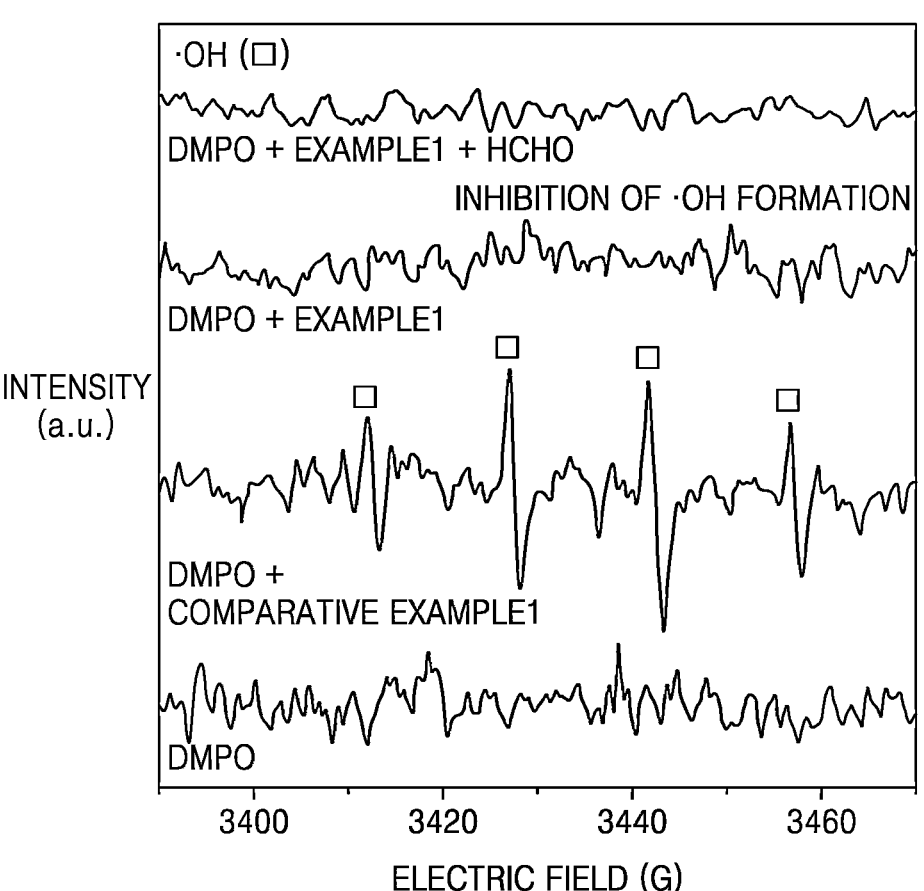
FIG. 11A shows an electron paramagnetic resonance (EPR) spectrum result obtained by analyzing an amount of an $\cdot$OH radical produced as an ROS for the $TiO_2$ photocatalyst of Comparative Example 1 and the $BiOI/TiO_2$ composite p-n heterojunction photocatalyst of Example 1.

Referring to FIGS. 10 and 11A, FIGS. 10 and 11A show that the BiOI/TiO$_2$ composite p-n heterojunction photocatalyst of Example 1 generates little if any detectable ·OH derived from oxidation of water as an ROS as compared with the TiO$_2$ photocatalyst of Comparative Example 1.

Figure 11B:
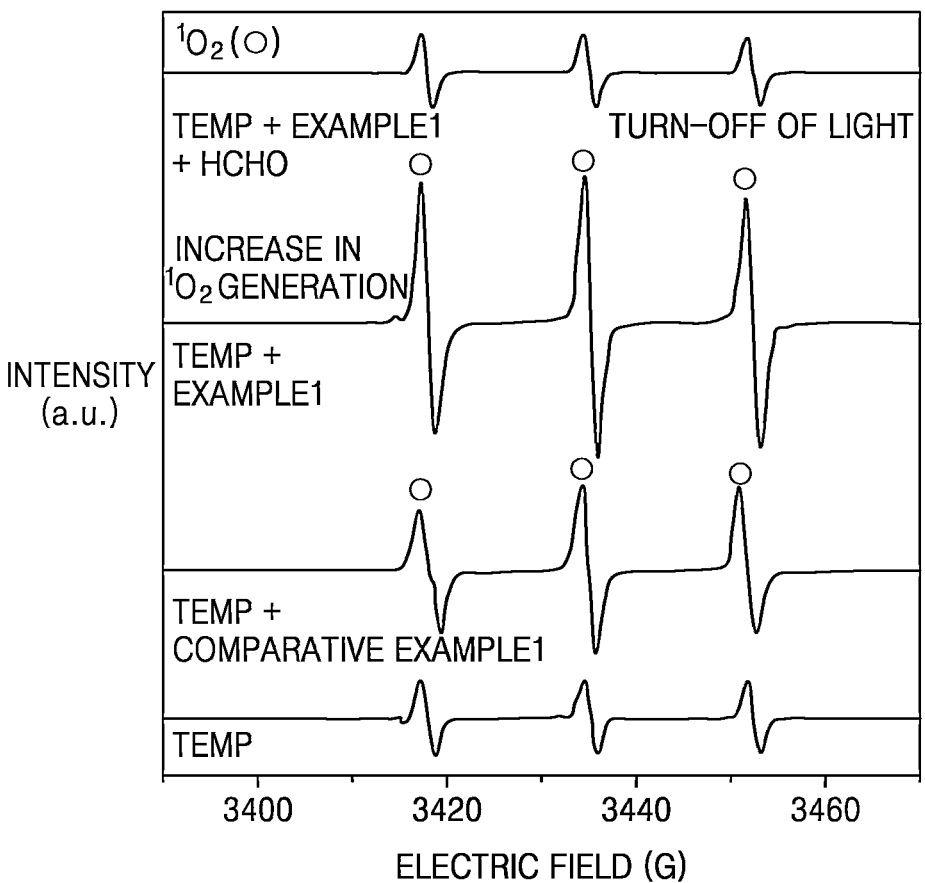
FIG. 11B shows an EPR spectrum result obtained by analyzing an amount of singlet oxygen ($^1O_2$) produced as an ROS for the $TiO_2$ photocatalyst of Comparative Example 1 and the $BiOI/Ti$ $TiO_2$ composite p-n heterojunction photocatalyst of Example 1.

Referring to FIG. 11B, FIG. 11B shows that the BiOI/TiO$_2$ composite p-n heterojunction photocatalyst of Example 1 generates greater amounts of $^1$O$_2$ derived from oxygen as compared with the TiO$_2$ photocatalyst of Comparative Example 1.

Referring to FIGS. 11A and 11B, the data is consistent when after formaldehyde (HCHO) is added to the BiOI/TiO$_2$ composite p-n heterojunction photocatalyst of Example 1, a production amount of $^1$O$_2$ decreases rapidly, which is consistent with $^1$O$_2$ is a main ROS that reacts with formaldehyde.

Evaluation Example 4: Evaluation of Movable $^1$O$_2$ Monitoring

Movable $^1$O$_2$ monitoring was evaluated on the TiO$_2$ photocatalyst of Comparative Example 1, the BiOI/TiO$_2$ composite p-n heterojunction photocatalyst of Example 1, Reference Example 1 (not including a photocatalyst), and Reference Example 2 (in which the BiOI/TiO$_2$ composite p-n heterojunction photocatalyst of Example 1 was not irradiated with UV light). The results are shown in FIG. 12B.

Figure 12A:
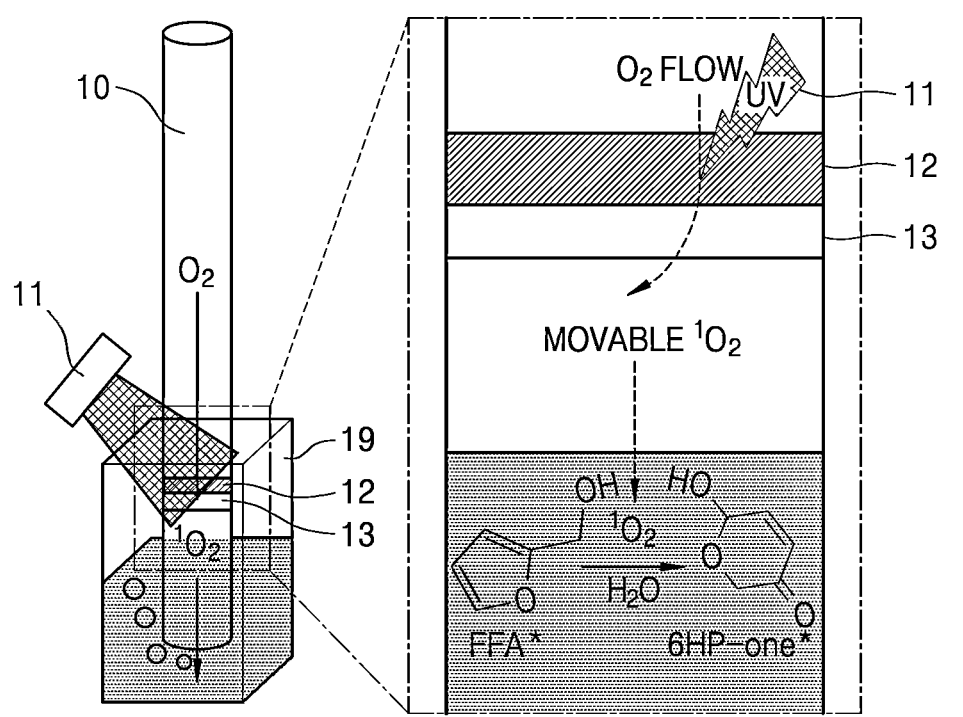
FIG. 12A schematically illustrates an experimental device for a movable $^1O_2$ monitoring experiment according to Evaluation Example 4.

For a movable $^1$O$_2$ monitoring experiment, an experimental device was designed and is schematically shown in FIG. 12A. A quartz tube 10 was disposed in a reactor 19, and hydrophobic quartz wool 13 and a sample of the TiO$_2$ photocatalyst of Comparative Example 1, the BiOI/TiO$_2$ composite p-n heterojunction photocatalyst of Example 1, Reference Example 1, and Reference Example 2 were each positioned atop the wool.

Oxygen gas (or a gas including oxygen) was allowed to flow down the quartz tube 10 to a surface of a solution 12 including 15 mg of each sample at a flow rate of 120 ml/min. 4 ml of 100 µM furfuryl alcohol (FFA) was used as a trapping solution for movable $^1$O$_2$. A distance between each sample and the trapping solution was 0.5 cm. UV light was used to irradiate the sample in the reactor 19 using a 365 nm UV LED 11 (manufactured by Fiber Optics Korea Co., Ltd.) having a light intensity of 50 mW/cm$^2$. 6-hydroxy-(2H)-pyran-3-one (6 HP-one), which is a product from a reaction between FFA and $^1$O$_2$, and FFA were analyzed using a Supelco LC-18 column and high-performance liquid chromatography (HPLC, e2695 manufactured by Waters Corporation) with a UV-visible detector.

Figure 12B:
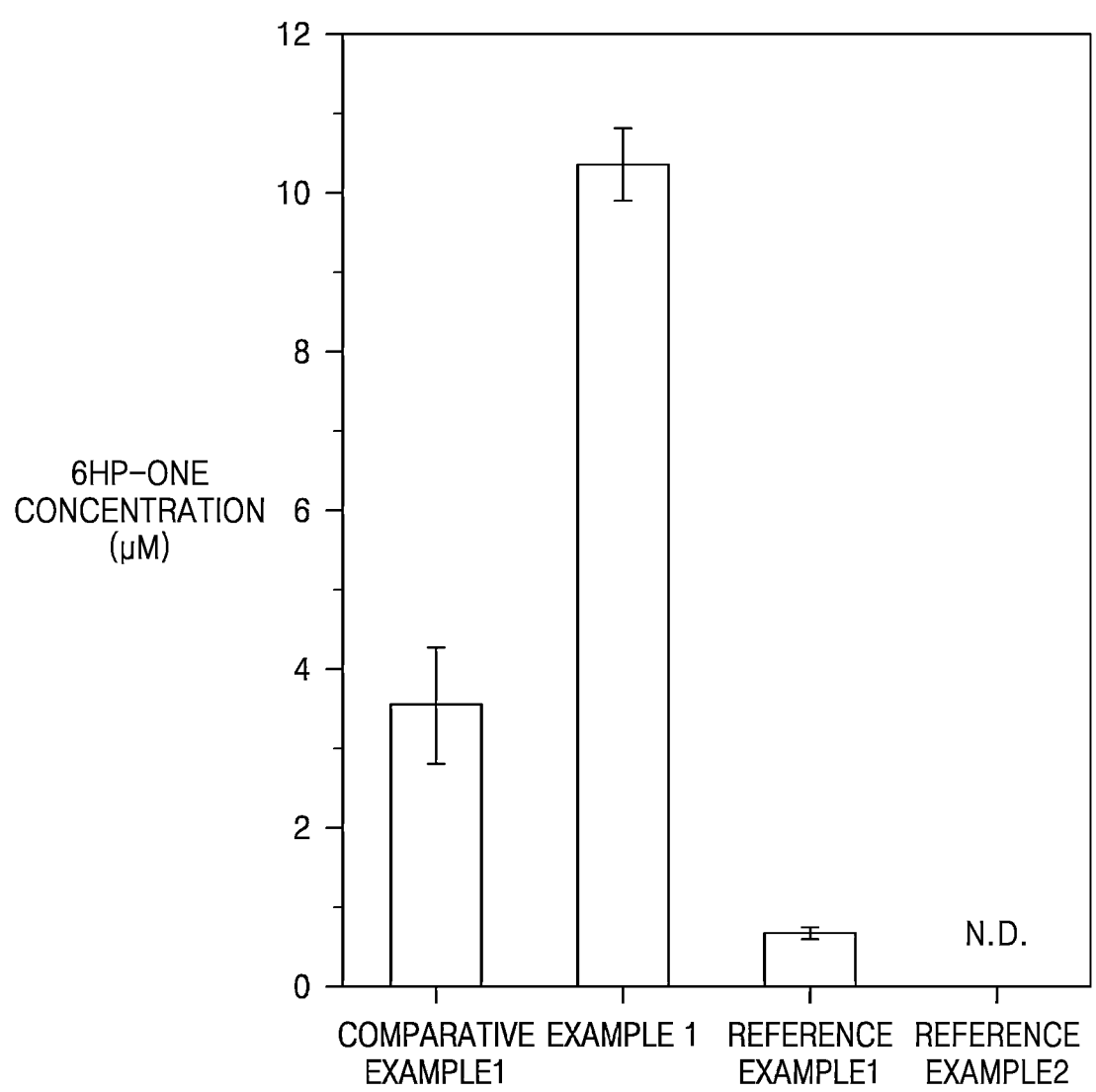
FIG. 12B is a bar graph showing a concentration of 6-hydroxy-(2H)-pyran-3-one (6 HP-one) for the $TiO_2$ photocatalyst of Comparative Example 1, the $BiOI/TiO_2$ composite p-n heterojunction photocatalyst of Example 1, Reference Example 1 (not including a photocatalyst), and Reference Example 2 ($BiOI/TiO_2$ photocatalyst of Example 1 not irradiated with UV light)

Referring to FIG. 12B, the experiment confirms that the ROS generated by the BiOI/TiO$_2$ composite of Example 1 is $^1$O$_2$, and the BiOI/TiO$_2$ photocatalyst of Example 1 generates a greater amount of $^1$O$_2$ in air as compared to the TiO$_2$ photocatalyst of Comparative Example 1, Reference Example 1 (not including the photocatalyst), and Reference Example 2 (BiOI/TiO$_2$ of Example 1 with no irradiation). In addition, it was confirmed from Reference Example 1 and Reference Example 2 that movable $^1$O$_2$ in the air is generated by a photoreaction of a photocatalyst.

Evaluation Example 5: HCHO Decomposition Experiment-Evaluation of Photoconversion Efficiency and Photoconversion Rate Photoconversion efficiency and a photoconversion rate according to HCHO decomposition were evaluated on the TiO$_2$ photocatalyst of Comparative Example 1 and the BiOI/TiO$_2$ composite p-n heterojunction photocatalysts of Examples 1, 2, 3, and 4. The results thereof are shown in FIGS. 18B, and the bar plots 19B and 19C.

Figure 18A:
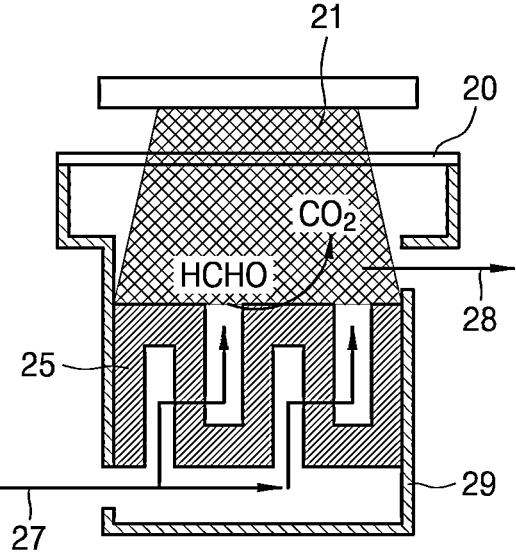
FIG. 18A is a schematic representation of a Teflon reactor used to obtain photoconversion efficiency of HCHO decomposition according to Evaluation Example 5.
Figure 18B:
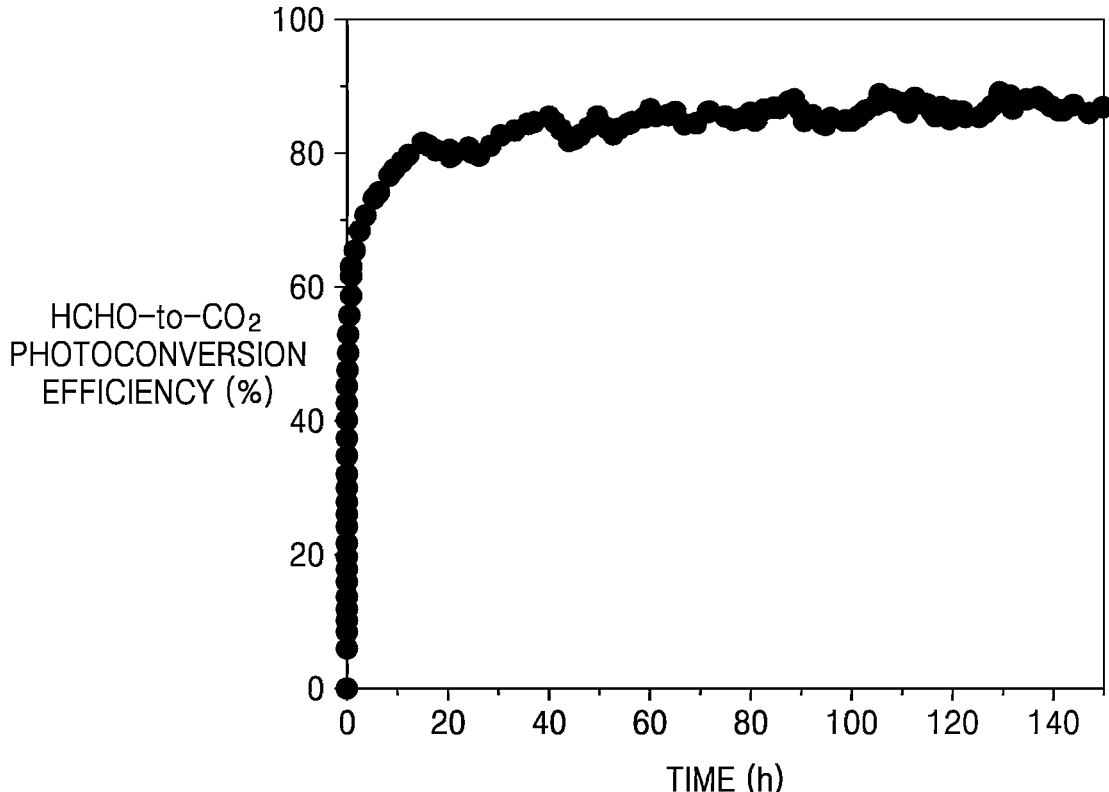
FIG. 18B shows data for HCHO decomposition photoconversion efficiency over time for the $BiOI/TiO_2$ composite p-n heterojunction photocatalyst of Example 1.

To obtain photoconversion efficiency a HCHO decomposition experiment was designed and is schematically shown in FIG. 18A. A Teflon reactor 29 equipped with an optically polished quartz window 20 and a total gas flow rate of 10 L/min was used in the experiment. The Teflon reactor 29 includes an LED light 21, a photocatalyst filter 25, a gas inlet 27, and a gas outlet 28.

The BiOI/TiO$_2$ composite p-n heterojunction photocatalyst of Example 1 was positioned below the quartz window 20. HCHO was supplied by vaporizing a paraformaldehyde powder (obtained from Sigma-Aldrich Co.) with a N$_2$ carrier gas. Concentrations of HCHO and CO$_2$ were measured using a real-time gas analysis FT-IR spectrometer (Titan 14001-E manufactured by MIDAC Corporation). A gaseous mixture (20% O$_2$ and 80% N$_2$) with a flow rate of 500 mL/min synthetic air containing 20 ppm HCHO and designated humidity was supplied to the reactor 29. UV light was irradiated onto a photocatalyst sample in the reactor 29 using a 365 nm UV LED (manufactured by Fiber Optics Korea Co., Ltd.) at a light intensity of 50 mW/cm² (irradiation area: 4 cm²).

Photoconversion efficiency ($X_{HCHO}$, %) of converting HCHO into $CO_2$ was calculated and obtained according to Equation 1 below.

$$X_{HCHO} = C_{CO2}/C_{HCHO} \times 100 (\%) \qquad \text{Equation 1}$$

In Equation 1, $X_{HCHO}$ denotes photoconversion efficiency of converting HCHO into $CO_2$, $C_{OO2}$ denotes a concentration of a $CO_2$ gas in the gas outlet 28, and $C_{HCHO}$ denotes a concentration of a HCHO gas in the gas inlet.

Referring to FIG. 18B, the $BiOI/TiO_2$ composite p-n heterojunction photocatalyst of Example 1 exhibits a photoconversion efficiency of 87% over at least 150 hours.

Figure 19A:
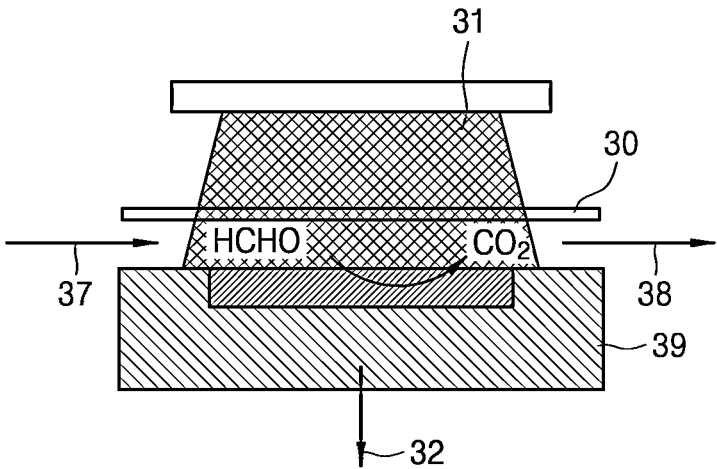
FIG. 19A is a schematic representation of a single-pass continuous flow reactor used to obtain a photoconversion rate of HCHO decomposition according to Evaluation Example 5.

To obtain a photoconversion rate a HCHO decomposition experiment was designed using a single-pass continuous flow reactor 39 as shown in FIG. 19A. The single-pass continuous flow reactor 39 includes a quartz window 30, light 31 from an LED, a photocatalyst sample positioned in reactor 39, a gas inlet 37, and a gas outlet 38. By using the $TiO_2$ photocatalyst of Comparative Example 1 and the $BiOI/TiO_2$ composite p-n heterojunction photocatalysts of Examples 1, 2, 3, and 4, a photoconversion rate was obtained as in the above-described photoconversion efficiency by measuring the decomposition of HCHO.

A photoconversion rate constant ($k_c$, $s^{-1}$) from HCHO to $CO_2$ was calculated and obtained according to Equations 2 and 3 below.

$$\tau = V/F = (S \times \delta)/F \qquad \text{Equation 2]}$$

In Equation 2, T denotes a residence time, V denotes an effective volume of a reactor, F denotes a flow rate of gas at the inlet 37, and 5 denotes an interval between a photocatalyst sample and a quartz window.

$$-\ln(1 - X_{CHO}) = k_c \tau \qquad \text{Equation 3}$$

In Equation 3, $X_{HCHO}$ denotes a photoconversion efficiency of converting HCHO into $CO_2$, and $k_c$ denotes a photoconversion rate constant from HCHO to $CO_2$.

Figure 19B:
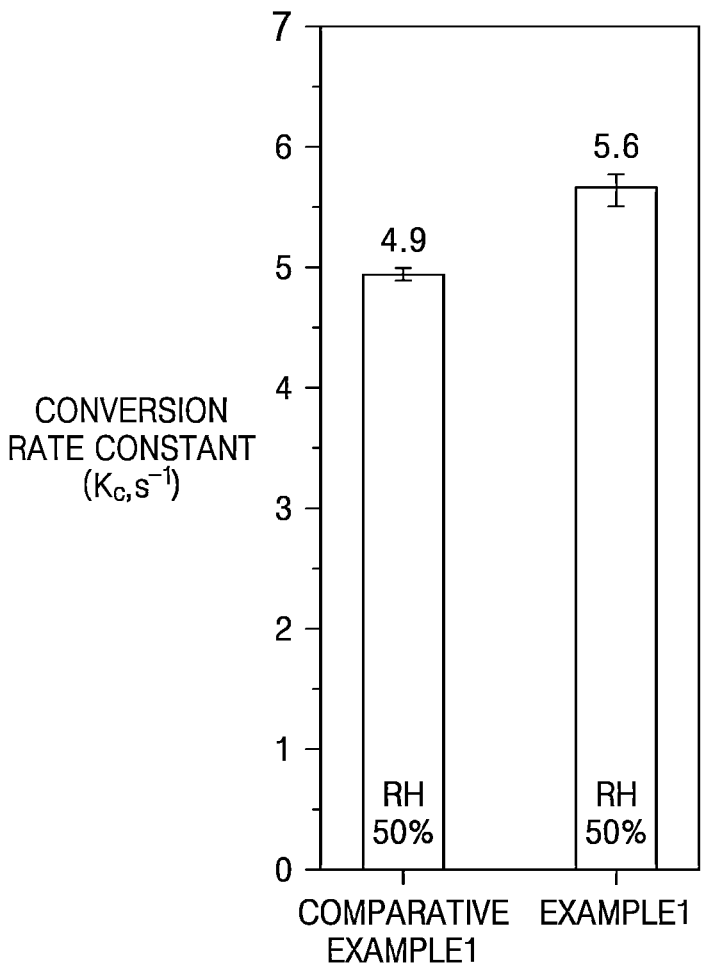
FIG. 19B is a bar graph showing photoconversion rate constants of the $TiO_2$ photocatalyst of Comparative Example 1 and the $BiOI/TiO_2$ composite p-n heterojunction photocatalyst of Example 1, under a relative humidity (RH) of 50%.

Referring to FIG. 19B, the $BiOI/TiO_2$ composite p-n heterojunction photocatalyst of Example 1 under a relative humidity (RH) of 50% has a photoconversion rate constant 1.2 times greater than that of the $TiO_2$ photocatalyst of Comparative Example 1.

Figure 19C:
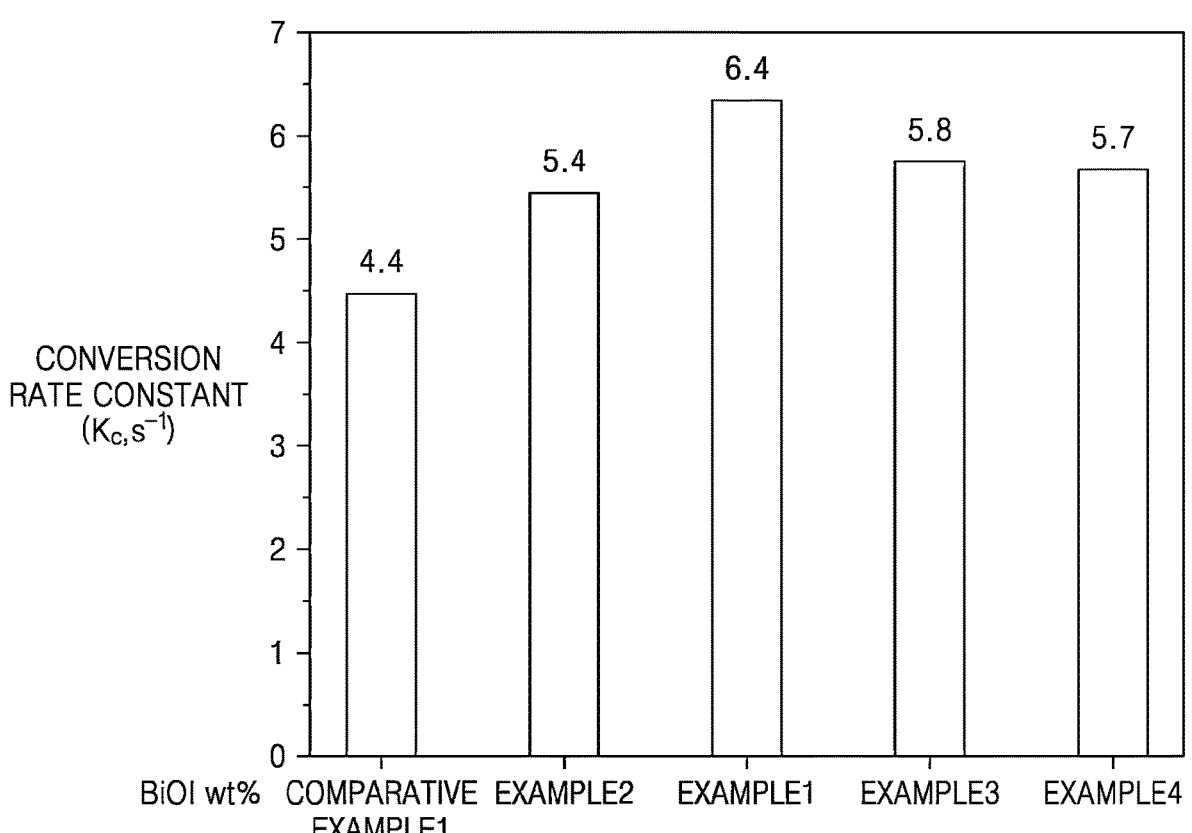
FIG. 19C is a bar graph showing photoconversion rate constants of the $TiO_2$ photocatalyst of Comparative Example 1 and $BiOI/TiO_2$ composite p-n heterojunction photocatalysts of Examples 1, 2, 3, and 4.

Referring to FIG. 19C, photoconversion rate constants of the $BiOI/TiO_2$ composite p-n heterojunction photocatalysts of Examples 1, 2, 3, and 4 are each greater than that of the $TiO_2$ photocatalyst of Comparative Example 1. Among the photoconversion rate constants, the photoconversion rate constant of the $BiOI/TiO_2$ composite p-n heterojunction photocatalyst of Example 1 is indicated to be the highest.

A p-n heterojunction photocatalyst according to one aspect includes a granule type composite including first compound particles, and second compound particles on at least a portion of surfaces of the first compound particles, wherein the composite has a size of about 0.9 μm to about 5 μm based on a major axis, a standard deviation of the size is about ±0.9 μm or less, and upon exposure to energy irradiation, the composite generates a ROC of singlet oxygen ($^1O_2$) to induce photolysis of gaseous pollutants. The p-n heterojunction photocatalyst generates movable singlet oxygen ($^1O_2$) having a relatively long lifetime and diffusion distance in air, and is shown to have high photoconversion efficiency (or decomposition efficiency) of converting gaseous pollutants (for example, HCHO) into $CO_2$.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope as defined by the following claims.

What is claimed is:

1. A p-n heterojunction photocatalyst comprising a composite, the composite comprising:

an agglomeration of a plurality of primary particles to provide a secondary first compound particles, wherein the particle size of the primary particles is in a range of about 20 nanometers to about 30 nanometers based on a major axis; and second compound particles on at least a portion of surfaces of the secondary first compound particle wherein the particle size of the secondary first compound particle is in a range of about 0.9 micrometers to about 5 micrometers based on a major axis, a standard deviation of the size is about ±0.9 micrometers or less, and upon exposure to energy irradiation, the composite generates a reactive oxygen species of singlet oxygen ($^1O_2$) to induce photolysis of gaseous pollutants.

2. The p-n heterojunction photocatalyst of claim 1, wherein the secondary first compound particle is an n-type compound, and the second compound particles are a p-type compound.

3. The p-n heterojunction photocatalyst of claim 1, wherein the secondary first compound particles comprises $TiO_2$, $BiVO_4$, $ZnO$, $WO_3$, $CdS$, $BaTiO_3$, or a combination thereof.

4. The p-n heterojunction photocatalyst of claim 1, wherein the second compound particles comprise $BiOI$, $Cu_2O$, $CuO$, $NiO$, $BiFeO_3$, $LaFeO_3$, $GaP$, or a combination thereof.

5. The p-n heterojunction photocatalyst of claim 1, wherein the second compound particles have an OH generation oxidation potential of about 1.97 V or less (vs NH-S) in a valence band.

6. The p-n heterojunction photocatalyst of claim 1, wherein the surfaces of the secondary first compound particle is negatively charged, and the second compound particles are positively charged and are self-assembled on the negatively charged surfaces of the secondary first compound particle through an electronic interaction to provide a granular composite.

7. The p-n heterojunction photocatalyst of claim 1, wherein the composite exhibits photolysis activity in an ultraviolet wavelength region.

8. The p-n heterojunction photocatalyst of claim 1, wherein the composite comprises titanium, and a peak of Ti2p binding energy, as measured by X-ray photoemission spectroscopy (NIPS), is shifted in a positive direction with respect to a peak of Ti2p binding energy of a $TiO_2$ photocatalyst.

9. The p-n heterojunction photocatalyst of claim 1, wherein the composite comprises bismuth, and a peak of Bi4f binding energy as measured by NIPS is shifted in a negative direction with respect to a peak of Bi4f binding energy of a $TiO_2$ photocatalyst.

10. The p-n heterojunction photocatalyst of claim 1, wherein a content of the plurality of primary particles is in a range of about 50 weight percent to about 95 weight percent, and a content of the second compound particles is in a range of about 5 weight percent to about 50 weight percent, based on a total weight of the composite.

11. An air purifier comprising a photocatalyst filter, the filter comprising the p-n heterojunction photocatalyst of claim 1.

12. A method of preparing the p-n heterojunction photocatalyst according to claim 1 the method comprising:

adding a plurality of primary compound particles to one or more second compound precursor solutions to obtain a mixture, wherein the particle size of the primary particles is in a range of about 20 nanometers to about 30 nanometers based on a major axis; and drying the mixture to prepare a composite comprising the agglomeration of the plurality of primary particles to provide the secondary first compound particles and the second compound particles on at least the portion of the surface of secondary first compound particle, wherein the composite has a size of about 1 micrometer to about 5 micrometers based on a major axis, a standard deviation of the size is about ±0.9 micrometers or less, and upon exposure to energy irradiation, the composite generates a reactive oxygen species of singlet oxygen ($^1O_2$) to induce photolysis of gaseous pollutants.

13. The method of claim 12, wherein the second compound precursor comprises $Bi(NO_3)_3$, $Bi(COOCH_3)_3$, KI, $Fe(NO_3)_3$, $La(NO_3)_3$, $FeSO_4$, $La_2(CO_3)_2(OH)_2$, $Fe_2O_3$, a hydrate thereof, or a combination thereof.

14. The method of claim 12, wherein the secondary first compound particles comprise $TiO_2$, $BiVO_4$, ZnO, $WO_3$, CdS, $BaTiO_3$, or a combination thereof.

15. The method of claim 12, wherein the adding the plurality of primary compound particles to the one or more second compound precursor solutions provide a content of the second compound particles in a range of about 5 weight percent to about 50 weight percent based on a total weight of the composite.

16. The method of claim 12, wherein the drying of the mixture is performed for about 12 hours to about 30 hours at a temperature of about 60° C. to about 100° C. under vacuum.

* * * * *